United States Patent
Labrecque et al.

(10) Patent No.: US 6,960,594 B2
(45) Date of Patent: Nov. 1, 2005

(54) THIOPHENE AND FURAN 2,5-DICARBOXAMIDES USEFUL IN THE TREATMENT OF CANCER

(75) Inventors: Denis Labrecque, Laval (CA); Serge Lamothe, Bolsbriand (CA); Marc Courchesne, Laval (CA); Laval Chan, Kirkland (CA); Giorgio Attardo, Laval (CA); Karen Meerovitch, Montreal (CA)

(73) Assignee: Shire BioChem Inc., Laval (CA)

( * ) Notice: Subject to any disclaimer, the term of this patent is extended or adjusted under 35 U.S.C. 154(b) by 0 days.

(21) Appl. No.: 10/046,396

(22) Filed: Jan. 16, 2002

(65) Prior Publication Data

US 2002/0137947 A1 Sep. 26, 2002

Related U.S. Application Data

(63) Continuation of application No. 09/736,027, filed as application No. PCT/IB99/01221 on Jan. 6, 2000, now abandoned.
(60) Provisional application No. 60/091,063, filed on Jun. 29, 1998.

(51) Int. Cl.[7] ............. A61K 31/505; A61K 31/34; C07D 409/12; C07D 239/02; C07D 333/22

(52) U.S. Cl. ............... 514/275; 514/461; 514/448; 549/71; 549/72; 549/485; 549/487; 544/333; 544/335; 546/280.4

(58) Field of Search .......................... 549/71, 72, 485, 549/487; 514/448, 461; 544/333, 335; 546/280.4

(56) References Cited

FOREIGN PATENT DOCUMENTS

| WO | WO 94/08577 | * | 4/1994 |
|---|---|---|---|
| WO | WO 97/37655 | * | 10/1997 |

* cited by examiner

*Primary Examiner*—Joseph K. McKane
*Assistant Examiner*—Ebenezer Sackey
(74) *Attorney, Agent, or Firm*—Millen, White, Zelano, Branigan, P.C.

(57) ABSTRACT

A novel compound which inhibits certain integrins, particularly $\alpha_v$ integrins. Additionally, the novel compound may be used in a method of treating tumors or cancer which comprises administering a pharmaceutically effective amount of the compound to a patient. Additionally, the novel compound may be used in a method of inhibiting angiogensis. Finally, a method of producing the novel compound is disclosed.

53 Claims, No Drawings

THIOPHENE AND FURAN 2,5-DICARBOXAMIDES USEFUL IN THE TREATMENT OF CANCER

This application claims benefit of U.S. Provisional Application Ser. No. 60/091,063, filed Jun. 29, 1998.

This is a Continuation of application Ser. No. 09/736,027 filed Dec. 21, 2000 now abandoned, which in turn is a 371 of International Application PCT/IB99/01221 filed Jan. 6, 2000. The disclosure of the prior application(s) is hereby incorporated by reference herein in its entirety.

FIELD OF THE INVENTION

The present invention relates to compounds that inhibit certain integrins, particularly to compounds that inhibit $\alpha_v$ integrins.

BACKGROUND OF THE INVENTION

Integrins are a major family of adhesion receptors. They are produced by most cell types and are a means by which the cell senses its immediate environnement and responds to changes in extracellular matrix (ECM) composition. ECM is composed of structural and regulatory molecules, some of which include laminin, collagen, vitronectin and fibronectin, as well as a variety of proteoglycans. These molecules, in cooperation with cell surface receptors, not only provide the basis for structural support, but also contribute to the transmission of biochemical signals from the ECM to the cells interior. Thus, integrins are cell adhesion receptors capable of mediating cell-extracellular matrix and cell—cell interactions. Integrins are implicated in the regulation of cellular adhesion, migration, invasion, proliferation, angiogenesis, osteoclast bone resorption, apoptosis and gene expression (P. C. Brooks, DN&P, 10(8), 456–61, 1997).

The integrin family is composed of 15 $\alpha$ and 8 $\beta$ subunits that are contained in over twenty different $\alpha\beta$ heterodimeric combinations on cell surfaces. Each heterodimers have distinct cellular and adhesive specificities. Integrins bind to extracellular matrix proteins or cell surface molecules through short peptides sequences present in the ligands. Although some integrins selectively recognize a single extracellular matrix protein ligand, other bind to two or more ligands. Several integrins recognize the tripeptide Arg-Gly-Asp (RGD), whereas others recognize alternative short peptide sequences. Combinations of different integrins on cell surfaces allow cells to recognize and respond to a variety of different extracellular matrix proteins (J. A. Varner and D. A. Cheresh, Curr. Opin. Cell Biol., 8, 724–30, 1996).

The $\alpha_v$-series integrins are a major subfamily of integrins. As well as classically mediating cell attachement and spreading, $\alpha_v$ integrins are implicated in cell locomotion, in ligand-receptor internalisation, as virus co-receptors, in management of the extracellular protease cascades and as regulators of tumour progression, angiogenesis and apoptosis. The specificities of the five known $\alpha_v$-integrins, ($\alpha_v\beta_1$, $\alpha_v\beta_3$, $\alpha_v\beta_5$, $\alpha_v\beta_6$ and $\alpha_v\beta_8$ have been defined and they exclusively recognize ligands via the tripeptide sequence RGD, including vitronectin ($\alpha_v\beta_1$, $\alpha_v\beta_3$, $\alpha_v\beta_5$), fibronectin ($\alpha_v\beta_1$, $\alpha_v\beta_5$, $\alpha_v\beta_6$), von Willibrand factor ($\alpha_v\beta_3$), fibrinogen ($\alpha_v\beta_3$) and osteopontin ($\alpha_v\beta_3$) (F. Mitjans, J. Cell. Science, 108, 2825–38, 1995).

In disease, adhesive function is frequently compromised and results in tissue disorder, aberrant cell migration and dysregulation of signaling pathways. It is well known that alterations in the composition and integrity of the ECM can significantly influence cellular behavior, which in turn may have an impact on a number of pathological processes such as tumor neovascularization, restenosis, arthritis, tumor growth and metastasis. Thus, inhibiting the function of molecules that regulate these cellular events may have significant therapeutic benefit (P. C. Brooks, DN&P, 10(8), 456–61, 1997).

There are at least three major classes of reagents currently being developed as integrin antagonists, and these include antibodies (monoclonal, polyclonal and synthetic) and small synthetic peptides (synthetic cyclic RGD peptides), as well as a family of snake venom-derived proteins termed "disintegrins". The third major group of antagonists includes nonpeptide mimetics and organic-type compounds.

Integrin $\alpha_v\beta_3$, the most promiscuous member of the integrin family, mediates cellular adhesion to vitronecin, fibronectin, fibrinogen, laminin, collagen, von Willibrand factor, osteopontin and adenovirus penton base. Expression of this integrin enables a given cell to adhere to, migrate on, or respond to almost any matrix protein it may encounter.

Integrins of the $\alpha_v$ subfamily are implicated in tumour development. Integrin $\alpha_v\beta_3$ is minimally, if at all expressed on resting, or normal, blood vessels, but is significantly upregulated on vascular cells within human tumors. In particular, both vertical progression of the primary melanoma and distant metastases are characterized histologically by an increased expression of $\alpha_v\beta_3$ integrin (B. Felding-Habermann et al., J. Clin. Invest., 89, 2018–22, 1992). A study involving human malignant melanoma, an increasingly prevalent and aggressive skin cancer, reported the use of monoclonal antibodies to block the $\alpha_v$ integrin-ligand interaction which resulted in severely disrupting the development of the tumor (F. Mitjans et al., J. Cell Sci., 108, 2825–38, 1995).

Another important physiological role played by integrin $\alpha_v\beta_3$ in cancer is within the process of angiogenesis. Angiogenesis, the formation of new blood vessels, allows the cancer to spread and grow. It was shown that blood vessels involved in angiogenesis have enhanced expression of $\alpha_v\beta_3$ (P. C. Brooks et al., Science, 264, 569–571, 1994; C. J. Drake et al., J. Cell Sci., 108, 2655–61, 1995). It was also shown that preventing the $\alpha_v\beta_3$ integrin from binding to their ligands caused apoptosis (programmed cell death) in the endothelial cells of newly formed blood vessels and inhibited neovascularization (P. C. Brooks et al., Cell, 79, 1157–64, 1994; M. Christofidou-Solomidou et al., Am. J. Pathol., 151(40), 975–83, 1997; J. Luna, Lab. Invest., 75(4), 563–73, 1996). Thus, antagonists of integrin $\alpha_v\beta_3$ may provide a powerful therapeutic approach for the treatment of neoplasia or other diseases characterized by angiogenesis.

Another pathological process which involves $\alpha_v\beta_3$ is coronary restenosis. Surgical trauma and/or injury to blood vessels may lead to the stimulation of smooth muscle cells resulting in an increase migration and proliferation of these cells, which causes an occlusion in the vessel wall and prevents blood flow. Following arterial injury, it was shown that there was early upregulation of integrin $\alpha_v\beta_3$ at sites of cell accumulation within the vessel wall and that selective blockade of $\alpha_v\beta_3$ was an effective anti-restenotic strategy (S. S. Srivatsa et al., Cardiovascul. Res., 36, 408–28, 1997).

$\alpha_v$ integrins are especially interesting targets since they are implicated in many metabolic processes, such as angiogenesis, bone resorption, cellular migration and proliferation. Consequently, antagonists of $\alpha_v$ integrins have great therapeutic potential for diseases such as rheumatoid arthritis, psoriasis, eye diseases (diabetic retinopathy and macular degeneration), restenosis, neointimal hyperplasia, osteoporosis and more particurlarly against tumors, since they simultaneously strike at the developing tumor and at its blood supply (U.S. Pat. No. 5,843,906-WO 9736859/GD Searle & Co; EP 854140/Hoechst AG; WO 9733887-WO9637492/Du Pont Merck Pharm Co; WO 9744333-WO 9737655-WO 9532710-WO 9408577).

There is thus a constant need to find other antagonists of $\alpha_v$ integrins in order to provide additional modes of treatments for many diseases that still have no cure. The present invention satisfies this and other need.

SUMMARY OF THE INVENTION

The present invention comprises a novel compound that is an effective inhibitor of integrins, particularly $\alpha_v$ integrins such as $\alpha_v\beta_3$ and $\alpha_v\beta_5$. Particularly, the compound is of the following formula 1:

FORMULA 1

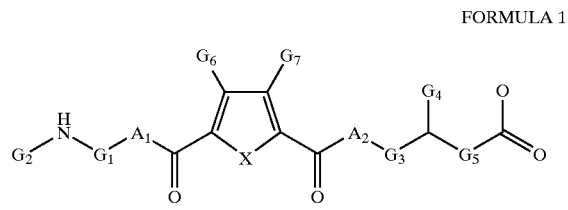

wherein X is selected from the group comprising O and S. Furthermore, $A_1$ and $A_2$ are individually selected from the group comprising O, S and N. $G_1$ is a $C_{1-4}$ alkyl chain, and $G_3$ and $G_5$ are $C_{0-4}$ alkyl chains. $G_2$ is selected from the group comprising:

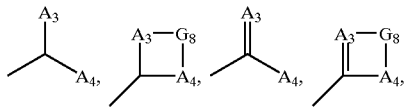

a $C_{1-4}$ alkyl-$C_{6-10}$-aryl, or H.

$A_3$ and $A_4$ are individually selected from the group comprising O, N, or S. $G_8$ is a $C_{1-4}$ alkyl chain. $G_4$ is a $C_{5-8}$ aryl, a $C_{5-8}$ arylsulfonylamino, or a $C_{5-8}$ arylamino. $G_6$ and $G_7$ are individually selected from the group comprising H, F, Cl, I, Br and a $C_{1-4}$ alkyl.

Other embodiments of the present invention include specific compounds and general formulas disclosed in the detailed description below.

Another aspect of the invention is a process for preparing a compound of formula 1. The method comprises preparing a compound according to Scheme A herein. Other embodiments of the invention include preparation of compounds according to any of the schemes or processes disclosed in the detailed description below.

Another aspect of the present invention includes a method for treating cancer comprising administering a pharmaceutically effective amount of the compound of formula 1 or any compound or formula disclosed in the detailed description to a patient. Other embodiments of the invention include methods of treatment as set forth in the detailed description.

Yet another aspect of the present invention includes a method for treating a tumor comprising administering a pharmaceutically effective amount of the compound of formula 1 or any compound or formula disclosed in the detailed description to a patient.

Yet another aspect of the present invention includes a method for inhibiting angiogenesis comprising administering a pharmaceutically effective amount of the compound of formula 1 or any compound or formula disclosed in the detailed description to a patient.

Yet another aspect of the present invention includes a method for inhibiting an $\alpha_v$ integrin comprising administering a pharmaceutically effective amount of the compound of formula 1 or any compound or formula disclosed in the detailed description to a patient.

DETAILED DESCRIPTION OF THE INVENTION

The present invention comprises a novel compound that is and effective inhibitor of integrins including $\alpha_v$ integrins as well as an effective medicament for the inhibition of angiogenesis and thereby treatment of cancer.

Particularly, the compound is of formula 1 wherein X is selected from the group comprising O and S. $A_1$ and $A_2$ are individually selected from the group comprising O, S and N. $G_1$ is a $C_{1-4}$ alkyl chain, and $G_3$ and $G_5$ are $C_{0-4}$ alkyl chains. $G_2$ is selected from the group comprising:

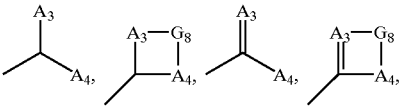

a $C_{1-4}$ alkyl $C_{5-8}$ aryl or H.

$A_3$ and $A_4$ are individually selected from the group comprising O, N, or S. $G_8$ is a $C_{1-4}$ alkyl chain. $G_4$ is a $C_{5-8}$ aryl, a $C_{5-8}$ arylsulfonylamino, or a $C_{5-8}$ arylamino. $G_6$ and $G_7$ are individually selected from the group comprising H, F, Cl, I, Br & a $C_{1-4}$ alkyl.

In another embodiment, the compound is defined according to formula 1 above except X is S.

In yet another embodiment, the compound is defined according to formula 1 above except X is O.

In yet another embodiment, the compound is defined according to formula 1 above except $A_1$ is a N.

In yet another embodiment, the compound is defined according to formula 1 above except $A_1$ is an O.

In yet another embodiment, the compound is defined according to formula 1 above except $A_2$ is a N.

In yet another embodiment, the compound is defined according to formula 1 above except $A_2$ is an O.

In yet another embodiment, the compound is defined according to formula 1 above except $G_1$ is —$(CH_2)_0$—.

In yet another embodiment, the compound is defined according to formula 1 above except $G_1$ is a $C_1$ alkyl.

In yet another embodiment, the compound is defined according to formula 1 above except $G_1$ is $C_2$ alkyl.

In yet another embodiment, the compound is defined according to formula 1 above except $G_1$ is $C_3$ alkyl.

In yet another embodiment, the compound is defined according to formula 1 above except $G_3$ is $C_1$ alkyl.

In yet another embodiment, the compound is defined according to formula 1 above except $G_3$ is $C_2$ alkyl.

In yet another embodiment, the compound is defined according to formula 1 above except $G_5$ is $C_1$ alkyl In yet another embodiment, the compound is defined according to formula 1 above except $G_5$ is $C_2$ alkyl.

In yet another embodiment, the compound is defined according to formula 1 above except $G_2$ is selected from the group comprising:

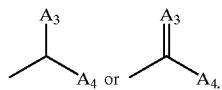

$A_3$ is selected from the group comprising O and N; $A_4$ is N.

In yet another embodiment, the compound is defined according to formula 1 above except $G_2$ is represented as follows:

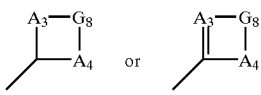

wherein $A_3$ and $A_4$ are individually selected from the group comprising N or O and $G_8$ is a $C_{2-3}$ alkyl.

In yet another embodiment, the compound is defined according to formula 1 above except —N-$G_2$ forms a guanidino containing moiety.

In yet another embodiment, the compound is defined according to formula 1 above except —N-$G_2$ forms a urea containing moiety.

In yet another embodiment, the compound is defined according to formula 1 above except $G_4$ is a $C_{-8}$ aryl.

In yet another embodiment, the compound is defined according to formula 1 above except $G_4$ is a $C_{5-8}$ arylsulfonylamino.

In yet another embodiment, the compound is defined according to formula 1 above except $G_4$ is an unsubstituted $C_{5-8}$ arylsulfonylamino.

In yet another embodiment, the compound is defined according to formula 1 above except $G_4$ is an unsubstituted $C_{5-8}$ arylamino.

In yet another embodiment, the compound is defined according to formula 1 above except $G_4$ is a substituted $C_{5-8}$ arylamino.

In yet another embodiment, the compound is defined according to formula 1 above except $G_4$ is a substituted phenylsulfonylamino.

In yet another embodiment, the compound is defined according to formula 1 above except $G_4$ is phenyl.

In yet another embodiment, the compound is defined according to formula 1 above except $G_4$ is an amino pyrimidinyl.

In yet another embodiment, the compound is defined according to formula 1 above except $G_4$ is a substituted amino pyrimidinyl.

In yet another embodiment, the compound is defined according to formula 1 above except $G_6$ and $G_7$ are halogens.

In yet another embodiment, the compound is defined according to formula 1 above except $G_6$ and $G_7$ are both fluorine.

In yet another embodiment, the compound is defined according to formula 1 above except $G_6$ and $G_7$ are the same.

In another embodiment, the compound is defined according to the following formula 2:

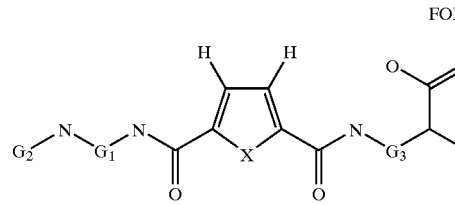

FORMULA 2 wherein X is S, $G_1$ and $G_3$ are $C_{-4}$ alkyl chains and $G_4$ is selected from the group comprising $C_{5-8}$ arylsulfonylamino, $C_{5-8}$ aryl, $C_{5-8}$ arylamino.

$G_2$ is represented as follows:

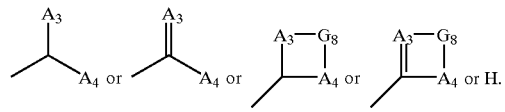

Particularly, $A_3$ is selected from the group comprising O, S and N; $A_4$ is N.

In another embodiment, the compound is according to formula 2, where X is O or S and $G_2$ is represented by the formula:

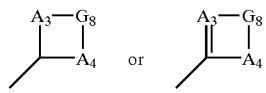

$A_3$ is selected from the group comprising O, S and N; $A_4$ is N. $G_8$ is a $C_{1-4}$ alkyl chain. Additionally, $G_4$ is selected from the group comprising $C_{5-8}$ arylsulfonylamino, $C_{5-8}$ aryl, $C_{5-8}$ arylamino. $G_1$ and $G_3$ are $C_{1-4}$ alkyl chains.

In another embodiment, the compound is defined according to formula 2 above except X is S.

In yet another embodiment, the compound is defined according to formula 2 above except X is O.

In yet another embodiment, the compound is defined according to formula 2 above except $A_1$ is N.

In yet another embodiment, the compound is defined according to formula 2 above except $A_1$ is an O.

In yet another embodiment, the compound is defined according to formula 2 above except $A_2$ is a N.

In yet another embodiment, the compound is defined according to formula 2 above except $A_2$ is an O.

In yet another embodiment, the compound is defined according to formula 2 above except $G_1$ is —$(CH_2)_0$—.

In yet another embodiment, the compound is defined according to formula 2 above except $G_1$ is a $C_1$ alkyl.

In yet another embodiment, the compound is defined according to formula 2 above except $G_1$ is a $C_2$ alkyl.

In yet another embodiment, the compound is defined according to formula 2 above except $G_1$ is a $C_3$ alkyl.

In yet another embodiment, the compound is defined according to formula 2 above except $G_3$ is a $C_1$ alkyl.

In yet another embodiment, the compound is defined according to formula 2 above except $G_3$ is a $C_2$ alkyl.

In yet another embodiment, the compound is defined according to formula 2 above except $G_5$ is a $C_1$ alkyl.

In yet another embodiment, the compound is defined according to formula 2 above except $G_5$ is a $C_2$ alkyl.

In yet another embodiment, the compound is defined according to formula 2 above except $G_2$ is represented as follows:

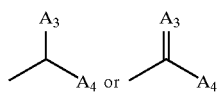

wherein $A_3$ is selected from the group comprising O, S and N and $A_4$ is N.

In yet another embodiment, the compound is defined according to formula 2 above except $G_2$ is represented as follows:

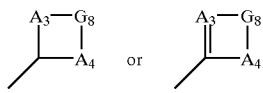

wherein $A_3$ and $A_4$ are individually selected from the group comprising N or O and $G_8$ is a $C_{2-3}$ alkyl chain.

In yet another embodiment, the compound is defined according to formula 2 above except —N-$G_2$ forms a guanidino containing moiety.

In yet another embodiment, the compound is defined according to formula 2 above except —N-$G_2$ forms a ureido containing moiety.

In yet another embodiment, the compound is defined according to formula 2 above except —N-$G_2$ forms is a cyclic guanidino containing moiety.

In yet another embodiment, the compound is defined according to formula 2 above except wherein —N-$G_2$ forms a cyclic urea containing moiety.

In yet another embodiment, the compound is defined according to formula 2 above except $G_4$ is phenylsulfonylamino.

In yet another embodiment, the compound is defined according to formula 2 above except $G_4$ is phenyl.

In yet another embodiment, the compound is defined according to formula 2 above except $G_6$ and $G_7$ are halogens.

In yet another embodiment, the compound is defined according to formula 2 above except $G_6$ and $G_7$ are both fluorine.

In yet another embodiment, the compound is defined according to formula 2 above except $G_6$ and $G_7$ are the same.

In another embodiment, the compound is represented by the following formula 3:

FORMULA 3

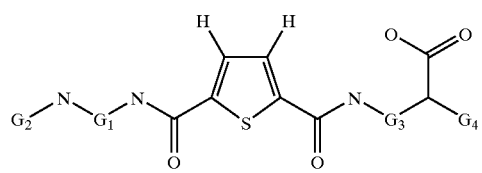

wherein $G_2$ is selected from the group comprising:

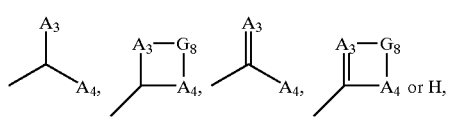

wherein $A_3$ and $A_4$ are individually selected from the group comprising O, N, or S and $G_8$ is a $C_{1-4}$ alkyl chain. Furthermore, $A_3$ is selected from the group comprising O, S and N, $A_4$ is N. $G_4$ is a $C_{5-8}$ arylsulfonylamino. $G_1$ and $G_3$ are $C_{1-4}$ alkyl chains.

In another embodiment, the compound is according to the above formula 3, wherein $G_2$ is selected from the group comprising:

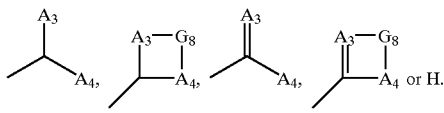

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. G4 is a $C_{5-8}$ aryl. $G_1$ and $G_3$ are $C_{1-4}$ alkyl chains.

In another embodiment, the compound is according to the above formula 3, wherein $G_2$ is selected from the group. comprising:

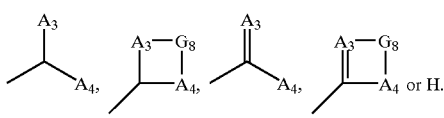

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. $G_4$ is phenylsulfonylamino. $G_1$ and $G_3$ are $C_{1-4}$ alkyl chains.

In another embodiment, the compound is according to the above formula 3, wherein $G_2$ is selected from the group comprising:

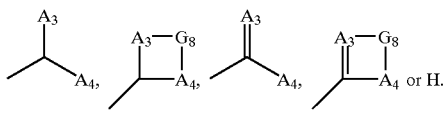

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. $G_4$ is an aminopyrimidinyl. $G_1$ and $G_3$ are $C_{1-4}$ alkyl chains.

In another embodiment, the compound is according to the above formula 3, wherein $G_2$ is selected from the group comprising:

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. $G_4$ is selected from the group comprising a phenylsulfonylamino, phenyl, or an aminopyrimidinyl.

In another embodiment, the compound is according to the above formula 3, wherein $G_2$ is selected from the group comprising:

$A_3$ and $A_4$ are individually selected from the group comprising O, N, or S. $G_8$ is a $C_{1-4}$ alkyl chain.

Furthermore, $A_3$ is selected from the group comprising O, S and N; $A_4$ is N. $G_4$ is selected from the group comprising phenylsulfonylamino, aryl, or an aminopyrimidinyl. In another embodiment, the compound is according to the above formula 3, wherein $G_2$ is selected from the group comprising:

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. $G_4$ is selected from the group comprising phenylsulfonylamino, a $C_{5-8}$ aryl, or an aminopyrimidinyl.

In another embodiment, the compound is according to the above formula 3, wherein $G_2$ is the following moiety:

$A_3$ and $A_4$ are individually selected from the group comprising O, N, or S. $G_8$ is a $C_{1-4}$ alkyl chain. Furthermore, $A_3$ is selected from the group comprising O, S and N; $A_4$ is N. $G_4$ is selected from the group comprising phenylsulfonylamino, a $C_{5-8}$ aryl, or an aminopyrimidinyl.

In another embodiment, the compound is according to formula 3, where $G_6$ and $G_7$ are halogens.

In another embodiment, $G_6$ and $G_7$ are the same.

In yet a more particular aspect of the invention, $G_6$ and $G_7$ are both fluorine.

In another embodiment, the compound is defined according to formula 3 above except X is S.

In yet another embodiment, the compound is defined according to formula 1 above except X is O.

In yet another embodiment, the compound is defined according to formula 3 above except $A_1$ is a N.

In yet another embodiment, the compound is defined according to formula 3 above except $A_1$ is an O.

In yet another embodiment, the compound is defined according to formula 3 above except $A_2$ is a N.

In yet another embodiment, the compound is defined according to formula 3 above except $A_2$ is an O.

In yet another embodiment, the compound is defined according to formula 3 above except $G_1$ is —$(CH_2)_0$—.

In yet another embodiment, the compound is defined according to formula 3 above except $G_1$ is a $C_1$ alkyl.

In yet another embodiment, the compound is defined according to formula 3 above except $G_1$ is a $C_2$ alkyl.

In yet another embodiment, the compound is defined according to formula 3 above except $G_1$ is a $C_3$ alkyl.

In yet another embodiment, the compound is defined according to formula 3 above except $G_3$ is a $C_1$ alkyl.

In yet another embodiment, the compound is defined according to formula 3 above except $G_3$ is a $C_2$ alkyl.

In yet another embodiment, the compound is defined according to formula 3 above except $G_5$ is a $C_1$ alkyl.

In yet another embodiment, the compound is defined according to formula 3 above except $G_5$ is a $C_2$ alkyl.

In yet another embodiment, the compound is defined according to formula 3 above except $G_2$ is selected from the group comprising:

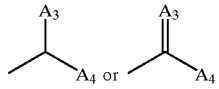

$A_3$ is selected from the group comprising O, S and N; $A_4$ is N.

In yet another embodiment, the compound is defined according to formula 3 above except $G_2$ is selected from the group comprising:

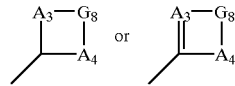

wherein $A_3$ and $A_4$ are individually selected from the group comprising N or O and $G_8$ is a $C_{2-3}$ alkyl chain.

In yet another embodiment, the compound is defined according to formula 3 above except —$N-G_2$ forms a guanidino containing moiety.

In yet another embodiment, the compound is defined according to formula 3 above except —$N-G_2$ forms a urea containing moiety.

In yet another embodiment, the compound is defined according to formula 3 above except —$N-G_2$ forms is a cyclic guanidino containing moiety.

In yet another embodiment, the compound is defined according to formula 3 above except wherein —$N-G_2$ forms a cyclic urea containing moiety.

In yet another embodiment, the compound is defined according to formula 3 above except $G_4$ is phenylsulfonylamino.

In yet another embodiment, the compound is defined according to formula 3 above except $G_4$ is phenyl.

In yet another embodiment, the compound is defined according to formula 3 above except $G_6$ and $G_7$ are halogens.

In yet another embodiment, the compound is defined according to formula 3 above except $G_6$ and $G_7$ are both fluorine.

In yet another embodiment, the compound is defined according to formula 3 above except $G_6$ and $G_7$ are the same.

Particular compounds according to the present invention include the following:

Compound I: 2'(S)5-(2'-Benzenesulfonylamino-2'-tert-butoxy carbonyl-ethylcarbamoyl)-thiophene-2-carboxylic acid.

Compound II: 2-Benzenesulfonylamino-3-{[5-(3-tert-butoxycarbonylamino-propylcarbamoyl)-thiophene-2-carbonyl]-amino}-propionic acid-tert-butyl ester.

Compound III: 2-Benzenesulfonylamino-3-{[5-(3-amino-propylcarbamoyl)-thiophene-2-carbonyl]-amino}-propionic acid, trifluoracetic acid salt.

Compound IV: 2-Benzenesulfonylamino-3-{[5-(3-guanidino-propylcarbamoyl)-thiophene-2-carbonyl]-amino}-propionic acid, trifluoracetic acid salt.

Compound V: 5-(3-tert-Butoxycarbonylamino-propylcarbamoyl)-thiophene-2-carboxylic acid.

Compound VI: 3-{[5-(3-tert-Butoxycarbonylamino-propylcarbamoyl)-thiophene-2-carbonyl]-amino}-3-phenyl-propionic acid tert-butyl ester.

Compound VII: 3-{[5-(3-Amino-propylcarbamoyl)-thiophene-2-carbonyl]-amino}-3-phenyl-propionic acid trifluoroacetic acid salt.

Compound VIII: 3-{[5-(3-guanidino-propylcarbamoyl)-thiophene-2-carbonyl]-amino}-3-phenyl-propionic acid.

Compound IX: (2S)2-Benzenesulfonylamino-3-{[5-(2-tert-butoxycarbonylamino-ethylcarbamoyl)-tiophen-2-carbonyl]-amino propionic acid tert-butyl ester.

Compound X: (2S)2-Benzenesulfonylamino-3-{[5-(2-amino-ethylcarbamoyl)-tiophen-2-carbonyl]-amino propionic acid trifluoroacetic acid salt.

Compound XI: (2S)2-Benzenesulfonylamino-3-{[5-(2-guanidinyl-ethylcarbamoyl)-thiophen-2-carbonyl]-amino propionic acid hydrochloride salt.

Compound XII: (2s) 2-Benzenesulfonylamino-3-(5-[2-(3-benzyl-ureido)-ethylcarbamoyl]-thiophen-2-carbonyl-amino) propionic acid.

Compound XIII: Dimethyl-2,5-thiophenedicarboxylic diester.

Compound XIV: 5-hydrazinocarbonyl-thiophene-2-carboxylic acid methyl ester.

Compound XV: 5-(N'-tert-Butoxycarbonyl-hydrazinocarbonyl)-thiophene-2-carboxylic acid methyl ester.

Compound XVI: 5-(N-tert-Butoxycarbonyl-hydrazinocarbonyl)-thiophene-2-carboxylic acid.

Compound XVII: 2S-Benzenesulfonylamino-3-{[5-(N-tert-Butoxycarbonyl-hydrazinocarbonyl)-thiophene-2-carbonyl]-amino{-propionic acid tert-butyl ester.

Compound XVIII: 2S-Benzenesulfonylamino-3-[(5-hydrazinocarbonyl-thiophene-2-carbonyl)-amino]-3-propionic acid trifluoroacetate.

Compound XIX: 2S-Benzenesulfonylamino-3-[(5-guanidino-aminocarbonyl-thiophene-2-carbonyl)-amino]-3-propionic acid trifluoroacetate.

Compound XX: (S)-3-((5-(2-Amino-ethylcarbamoyl)-furan-2-carbonyl)-amino)-2-benzenesulfonylamino-propionic acid trifluoroacetate.

Compound XXI: (s)-2-Benzenesulfonylamino-((5-(2-guanidino-ethylcarbamoyl)-furan-2-carbonyl)-amino)-propionic acid hydrochloride.

Compound XXIII: Thiophene-2,5-dicarboxylic acid monomethyl ester.

Compound XXIV: N,N'-Bis-(Boc)-N''-(2-Amino-ethyl)-guanidine.

Compound XXV: 3-tert-Butoxycarbonylamino-2-(pyrimidin-2-ylamino)-propionic acid methyl ester.

Compound XXVI: (3-Amino-2-(pyrimidin-2-ylamino)-propionic acid methyl ester bis hydrochloride salt.

Compound XXVII: 5-(2-(N,N'-Bis-(BOC)-guanidino)-ethylcarbamoyl)-thiophene-2-carboxylic acid methyl ester.

Compound XXXIX: 3-{[5-(2-(N,N'-Bis-(BOC)-guanidino)-ethylcarbamoyl)-thiophene-2-carbonyl]-amino}-2-(pyrimidin-2-ylamino)-propionic acid methyl ester.

Compound XXX: 3-{[5-(2-guanidino-ethylcarbamoyl)-thiophene-2-carbonyl]-amino}-2-(pyrimidin-2-ylamino)-propionic acid bis trifluoroacetic acid salt.

Compound XXXI: [2-(1-Oxy-pyridin-2-ylamino)-ethyl)]-carbamic acid tert-butyl.

Compound XXXII: [2-(Pyridin-2-ylamino)-ethyl]-carbamic acid tert-butyl ester.

Compound XXXIII: 5-[2-(Pyridin-2-ylamino)-ethylcarbamoyl]-thiophene-2-carboxylic acid methyl ester.

Compound XXXIV: 3-({5-[2-(Pyridin-2-ylamino)-ethylcarbamoyl]-thiophene-2-carbonyl}-amino)-2-(2,4,6-trimethyl-benzenesulfonylamino)-propionic acid methyl ester.

Compound XXXV: 3-({5-[2-(Pyridin-2-ylamino)-ethylcarbamoyl]-thiophene-2-carbonyl}-amino)-2-(2,4,6-trimethyl-benzenesulfonylamino)-propionic acid acetic acid salt.

Compound XXXVI: 2-Benzenesulfonylamino-3-({5-[(1H-benzoimidazol-2-ylmethyl)-carbamoyl]-thiophene-2-carbonyl-amino)-propionic acid.

Compound XXXVII: 3-({5-[(6-Amino-pyridin-3-ylmethyl)-carbamoyl]-thiophene-2-carbonyl}-amino)-2-benzenesulfonylamino-propionic acid tert-butyl ester.

Compound XXXVIII: 3-({5-[(6-Amino-pyridin-3-ylmethyl)-carbamoyl]-thiophene-2-carbonyl}-amino)-2-benzenesulfonylamino-propionic acid trifluoroacetic acid salt.

Compound XXXIX: [2-(Pyrimidin-2-ylamino)-ethyl]-carbamic acid-tert-butyl ester.

Compound XL: N,1-Pyrimidin-2-yl-ethane-1,2-diamine trifluoroacetic acid salt.

Compound XLI: 2-Benzenesulfonylamino-3-({5-[2-(pyrimidin-2-ylamino)-ethylcarbamoyl]-thiophene-2-carbonyl})-amino)-propionic acid tert-butyl ester.

Compound XLII: 2-Benzenesulfonylamino-3-({5-[2-(pyrimidin-2-ylamino)-ethylcarbamoyl]-thiophene-2-carbonyl}-amino)-propionic acid trifluoroacetic acid salt.

Compound XLIII: 2-Benzenesulfonylamino-3-({5-[2-(1,4,5,6-tetrahydro-pyrimidin-2-ylamino)-ethylcarbamoyl]-thiophene-2-carbonyl}-amino)-propionic acid, hydrochloride salt.

The term "alkyl" as used herein represents a straight or branched, saturated or unsaturated chain having a specified total number of carbon atoms (i.e. $C_2$ alkyl has two carbonatoms in the chain).

The term "phenyl" or "benzene" represent a six membered aromatic carbon containing ring whether or not the ring is a substituent group or otherwise.

The term "amino" includes primary amines i.e. $NH_2$, secondary amines i.e. NHR, or tertiary amines i.e. $N(R)_2$ wherein R is $C_{1-4}$ alkyl. Also encompassed by the term are quaternary amines such as $NH_3^+$.

The term "guanidino" refers to the following structure:

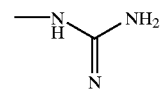

The term "guanidino containing moiety" refers to a moiety that has one carbon bound to three nitrogen.

The term "cyclic guanidino" refers to the following structure:

wherein Q is an alkyl.

The term "urea" refers generally to the following structure:

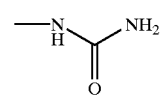

The term "urea containing moiety" refers to a moiety that contains a carbon bound to two nitrogen atoms and an oxygen atom.

The term "cyclic urea" refers to the following structure:

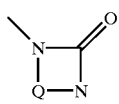

wherein Q is an alkyl.

The term "aryl" as defined herein refers to an aromatic ring having specified number of carbons (i.e. $C_2$ has two carbons) that may optionally be substituted with one or more heteroatoms selected from the group comprising O, N, or S.

The term "arylamino" refers to an aryl group, wherein the aryl group is covalently bonded to an adjacent element through a nitrogen atom.

The term "sulfonyl" refers to a compound with the following structure:

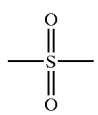

The above terms also includes salts, esters, and salts of esters of the above corresponding structures unless designated otherwise.

The term "arylsulfonyl" refers to an aryl group, wherein the aryl group is covalently bonded to an adjacent element through a sulfonyl (e.g. —$SO_2$—).

The term "phenylsulfonyl", refers to a phenyl ring, wherein the phenyl ring is covalently bonded to an adjacent element through a sulfonyl (e.g. —$SO_2$—)

The term "pyrimidinyl", represents a six membered aryl that contains two nitrogen atoms separated by carbon.

The present invention also includes methods of making compounds of formula 1 or any of the other formulas disclosed herein. Compounds of the present invention can be synthesized using conventional preparative steps and recovery methods known to those skilled in the art of organic chemistry. A synthetic route according to-one embodiment of the invention is illustrated in Scheme A and described as follows.

Referring to Scheme A, synthesis of compound A-8 is undertaken by reaction of compound A-1, which is dissolved in a solution containing a specified amount of anhydrous dimethyl formamide (DMF) and o-(7-azabenzotriazole-1-yl)-1,1,3,3-tetramethyluronium hexafluorophosphate (HATU), with compound A-2 to yield compound A-3. The resulting substituted 2,5-thiophene dicarboxylic acid is then coupled with compound A-4 using HATU in the presence of anhydrous DMF to give compound A-5. This product is then deprotected using a solution of dichloromethane and trifluoroacetic acid (TFA) to yield compound A-6. The resulting TFA salt is then added to a reaction mixture composed of distilled water, DMF, diisopropylethylamine (DIPEA) and 1H-pyrazole-1-carboxamidine hydrochloride (PCA) to give compound A-7. The resulting guanidino compound A-7 is reacted with benzyl isocyanate to give compound A-8.

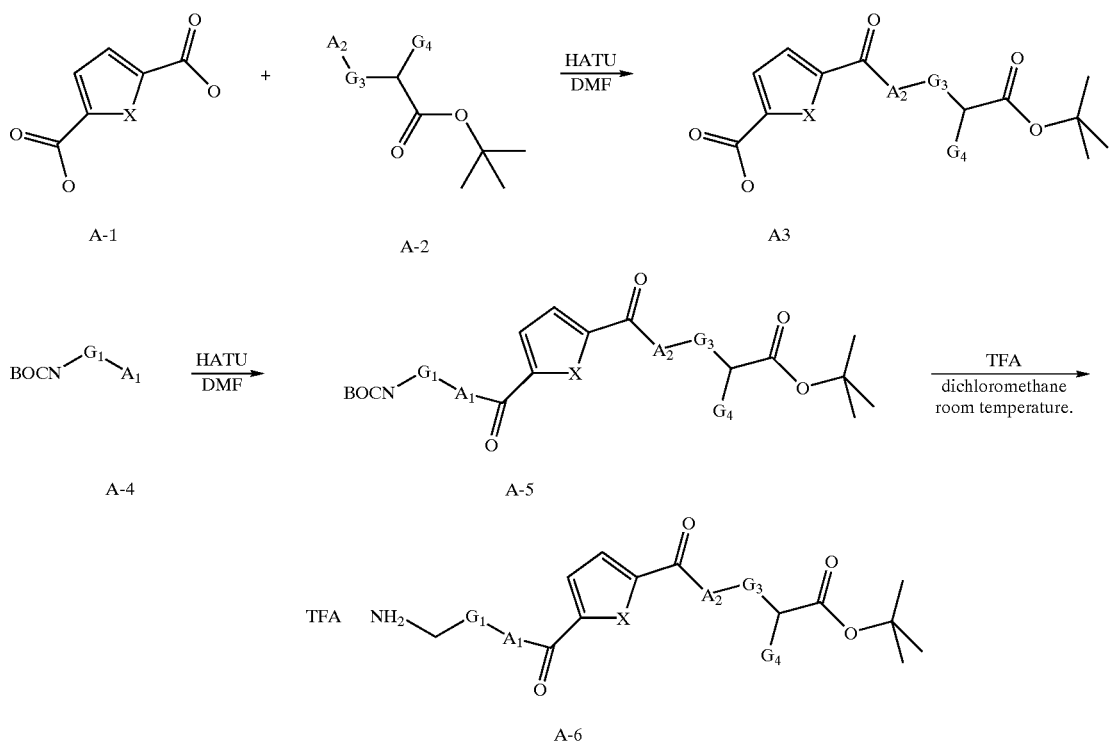

SCHEME A

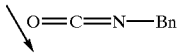

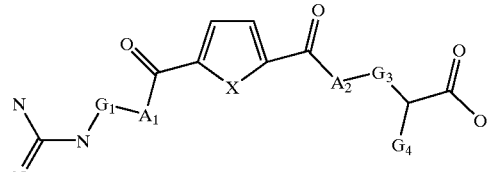

A-7

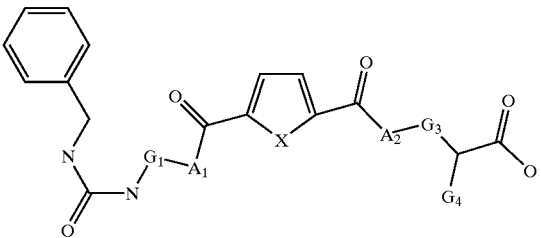

A-8

Another synthetic route, according to one embodiment of the present invention, is illustrated in Scheme B and described as follows.

Referring to Scheme B, synthesis of compound B-7 is undertaken by coupling compound B-1 with compound B-2 in anhydrous DMF using HATU. The resulting product B-3 is then reacted with compound B-4 in anhydrous DMF using HATU. The resulting disubstituted 2,5-thiophene dicarboxylic acid compound B-5 is then deprotected using a solution of dichloromethane and TFA to yield compound B-6. The resulting TFA salt is then added to a reaction mixture composed of distilled water, DMF, DIPEA and PCA to give the guanidino compound B-7.

SCHEME B

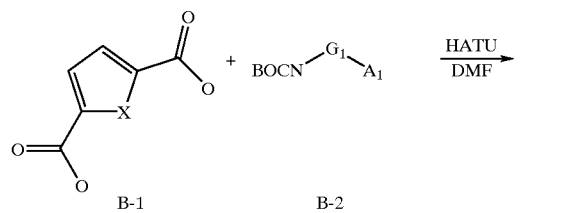

B-6

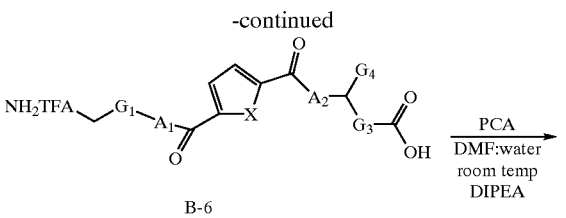

B-7

Another synthetic route according to one embodiment of the present invention is illustrated in Scheme C and described as follows.

Now referring to Scheme C, sodium hydride and iodomethane are sequentially added to a solution of compound C-1 in anhydrous DMF to yield compound C-2. The resulting dimethyl-2,5-thiophene diester is then reacted with hydrazine in the presence of anhydrous dioxane to produce compound C-3. The resulting hydrazinocarbonyl group is then protected using Di tert-butyl dicarbonate in the presence of DIPEA to yield compound C-4. The methyl ester group is then hydrolyzed with an aqueous LiOH solution to yield compound C-5. The resulting monocarboxylic acid is then added to a reaction mixture containing compound C-6, N-methylmorpholine (NMM) and HATU to produce compound C-7. The resulting phenylsulfonylamino thiophene is then deprotected using dichloromethane in TFA to yield compound C-8. The resulting compound is finally reacted with PCA compound to produce compound C-9.

SCHEME C

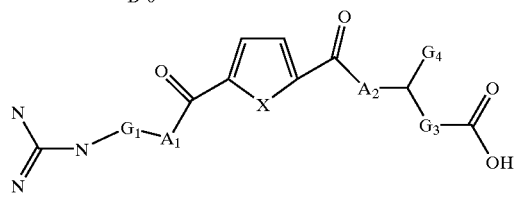

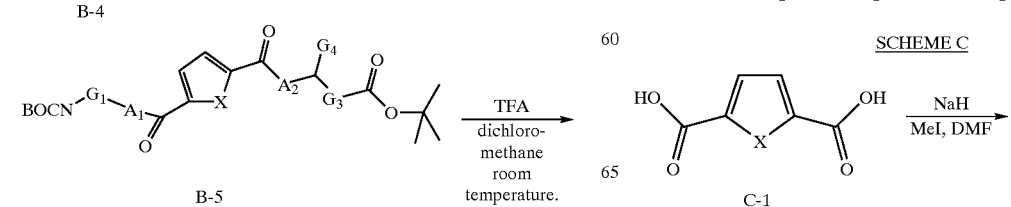

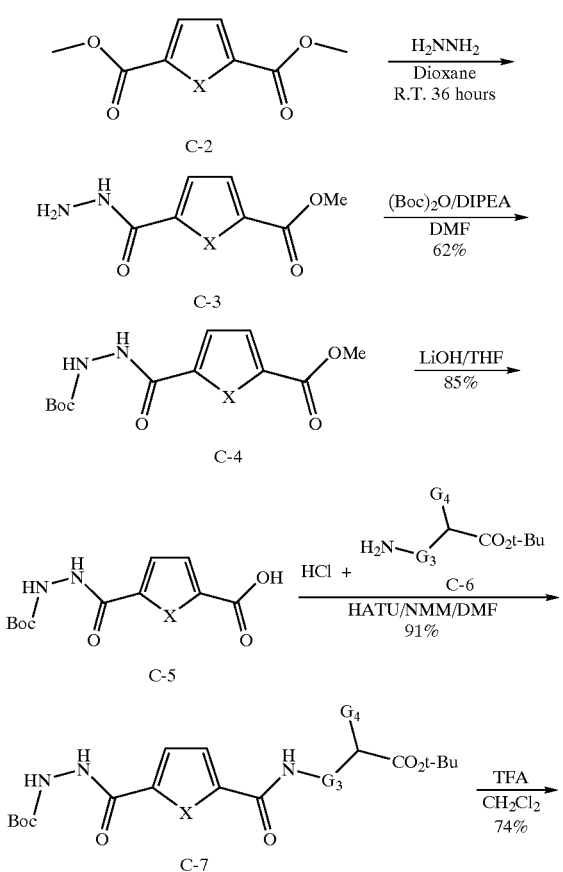

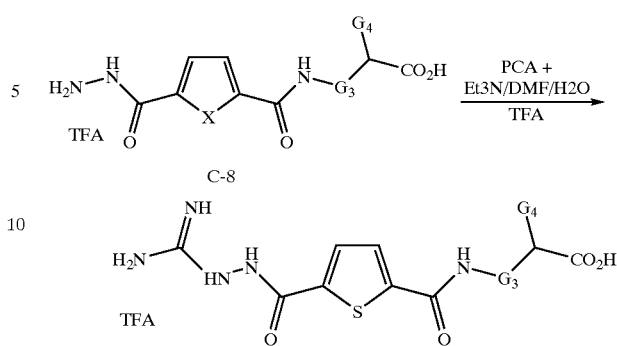

Another synthetic route according to one embodiment of the present invention is illustrated in Scheme D and described as follows.

Benzotriazole-1-yl-oxy-tris(dimethylamino)-phosphonium hexafluorophosphate (Bop reagent) is added to compound D1. After stirring for 20 min., a solution of compound D2 and D3 are sequentially added to yield compound D4. The resulting disubstituted thiophene is reacted with TFA in anhydrous dichloromethane to give compound D5. The resulting TFA salt is then reacted with CPA and DIPEA to produce compound D6. To a mixture of the resulting guanidinyl compound is added a portion of benzyl isocyanate to yield compound D7.

SCHEME D

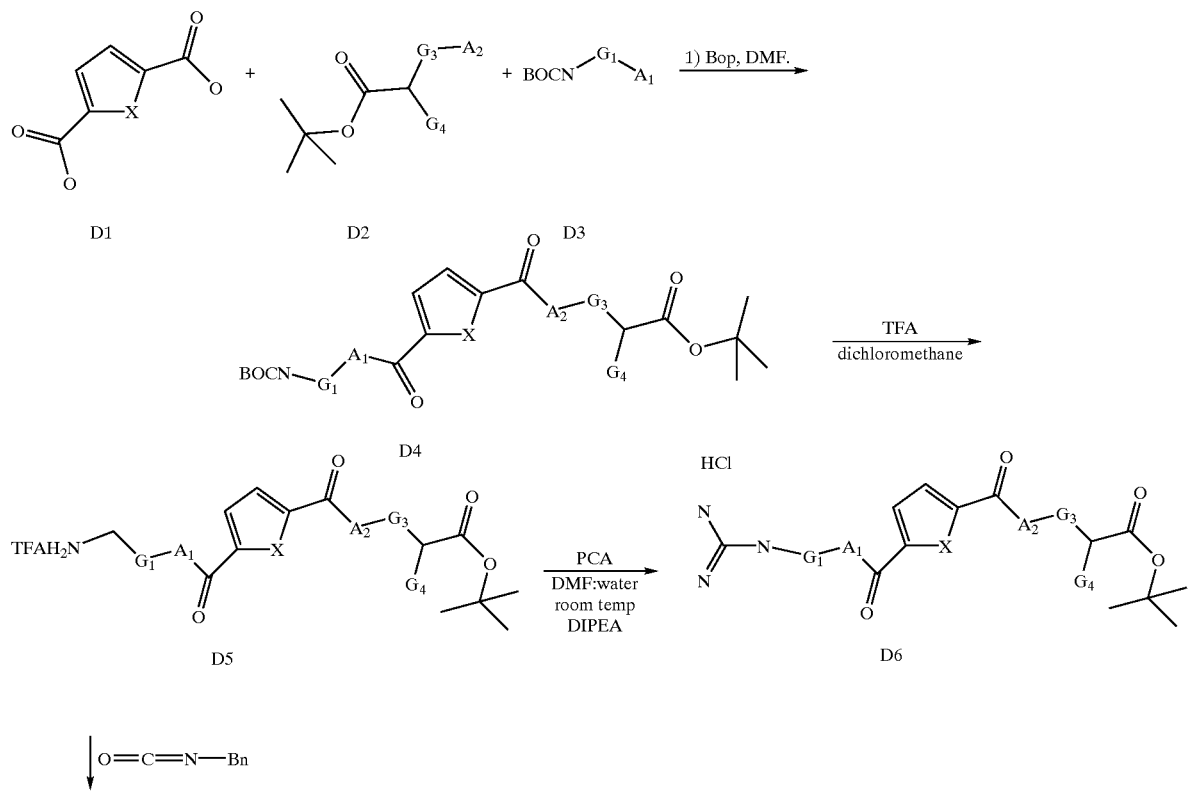

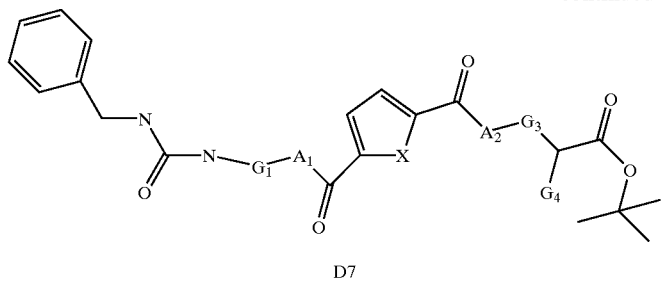

D7

Another synthetic route according to one embodiment of the present invention is illustrated in Scheme E and described as follows.

Referring to Scheme E, synthesis of compound E7 is undertaken by coupling compound E1 with compound E2 using HOBT and EDC. The resulting product E3 is then hydrolyzed with LiOH in THF to give the monocarboxylic acid compound E4. This product is then coupled with compound E5 in the presence of HOBT and EDC to produce compound E6. The resulting disubstituted 2,5-thiophene is then hydrolyzed with LiOH and converted to the TFA salt to yield compound E7.

Scheme E

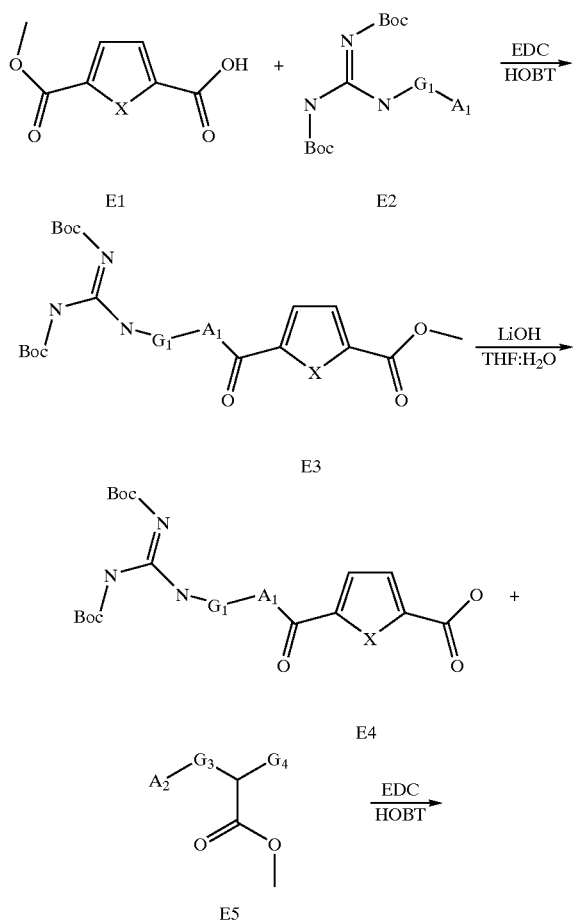

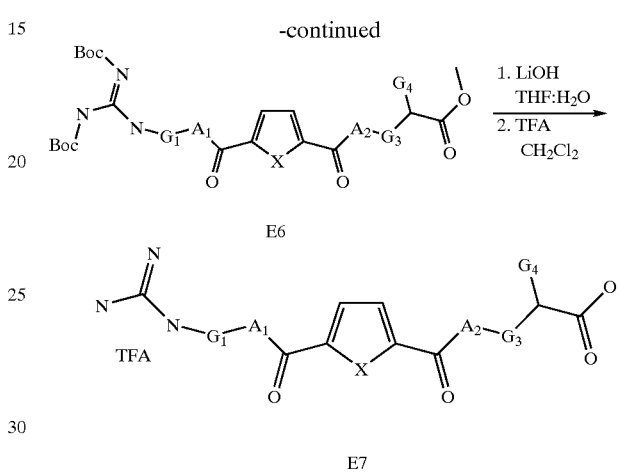

It will be appreciated by those skilled in the art that the compounds of formulas 1, 2 and 3 depending on the substituents, may contain one or more chiral centers and thus exist in the form of many different isomers, optical isomers (i.e. enantiomers) and mixtures thereof including racemic mixtures. All such isomers, enantiomers and mixtures thereof including racemic mixtures are included within the scope of the invention.

It will particularly be appreciated by a person of ordinary skill in the art that the above disclosed schemes A, B, and C cover both thiophene compounds, where X is S, and furan compounds, where X is O.

One embodiment of the present invention comprises a method for inhibiting an integrin using a compound of formula 1 or any compound or formula disclosed herein.

Another embodiment of the present invention comprises a method for inhibiting an $\alpha_v$ integrin using a compound of formula 1 or any compound or formula disclosed herein.

Another embodiment of the present invention comprises a method for inhibiting $\alpha_v\beta_3$ using a compound of formula 1 or any compound or formula disclosed herein.

In yet another embodiment of the present invention comprises a method for inhibiting $\alpha_v\beta_5$ using a compound of formula 1 or any compound or formula disclosed herein.

Another embodiment of the present invention comprises a method for inhibiting angiogenesis using a compound of formula 1 or any compound or formula disclosed herein.

Another embodiment of the present invention comprises a method for preventing a cell from binding to osteopontin using a compound of formula 1 or any compound or formula disclosed herein.

Another embodiment of the present invention comprises a method for preventing a cell from binding to fibronectin using a compound of formula 1 or any compound or formula disclosed herein.

Another embodiment of the present invention comprises a method for treating a tumor using a compound of formula 1 or any compound or formula disclosed herein. In another aspect of this invention, the tumor is a solid tumor.

Another embodiment of the present invention comprises a method for treating metastasis using a compound of formula 1 or any compound or formula disclosed herein.

Another embodiment of the present invention comprises a method for treating cancer using a compound of formula 1 or any compound or formula disclosed herein.

Another embodiment of the present invention comprises a method for treating foot and mouth disease using a compound of formula 1 or any compound or formula disclosed herein.

Another embodiment of the present invention comprises a method for treating osteoporosis using a compound of formula 1 or any compound or formula disclosed herein.

Another embodiment of the present invention comprises a method for treating restenosis using a compound of formula 1 or any compound or formula disclosed herein.

Another embodiment of the present invention comprises a method for treating ocular diseases using a compound of formula 1 or any compound or formula disclosed herein.

Another embodiment of the present invention comprises a method for treating heart diseases using a compound of formula 1 or any compound or formula disclosed herein.

Another embodiment of the present invention comprises a method for treating arthritis using a compound of formula 1 or any compound or formula disclosed herein.

Another embodiment of the present invention comprises a method for treating diseases in which abnormal neovascularization occurs using a compound of formula 1 or any compound or formula disclosed herein.

Another aspect of the present invention comprises using a compound of formula 1 or any compound or formula disclosed herein with at least one other anticancer agent or antiangiogenic agent.

Another embodiment of the present invention comprises using a compound of formula 1 or any compound or formula disclosed herein with at least one other chemotherapeutic agent.

One embodiment of the present invention comprises using a compound of formula 1 or any compound or formula disclosed herein with at least one other anticancer agent selected from the group consisting of alkylating agents, antitumor antibiotics, antimetabolites, biological agents, hormonal agents, nitrogen mustard derivatives and plant alkaloids.

Another embodiment of the present invention comprises using a compound of formula 1 or any compound or formula disclosed herein with at least one alkylating agent selected from the group consisting of busulfan, carboplatin, carmustine, semustine, sibiromycin, cisplatin, cyclophosphamide, decarbazine, ifosfamide, lomustine or strotozocin.

Another embodiment of the present invention comprises using a compound of formula 1 or any compound or formula disclosed herein with at least one antitumor antibiotic selected from the group consisting of bleomycin, dactinomycin, daunorubicin, doxorubicin, idonubicin, mitomycin-C and plicamycin.

Another embodiment of the present invention comprises using a compound of formula 1 or any compound or formula disclosed herein with at least one antimetabolite selected from the group consisting of cytarabines, prednisones, floxuridine, 5-fluorouracil, fludarabine, hydroxyureas, mercaptopurines, methotrexate and thioguanine.

Another embodiment of the present invention comprises using a compound of formula 1 or any compound or formula disclosed herein with at least one biological agent selected from the group consisting of aldeleukin, interferonα-2a, interferonα-2b, interferonα-n3, interferon8-1B and interleukin-2.

Another embodiment of the present invention comprises using a compound of formula 1 or any compound or formula disclosed herein with at least one hormonal agent selected from the group consisting of aminoglutethimide, anastrozole, flutamide, goserelin, megestrol, mitotane and tamoxifen.

Another embodiment of the present invention comprises using a compound of formula 1 or any compound or formula disclosed herein with at least one nitrogen mustard derivative selected from the group consisting of clorambucil, estramustine, michlorethamine, melphalan and thiotepa.

Another embodiment of the present invention comprises using a compound of formula 1 or any compound or formula disclosed herein with at least one plant alkaloide selected from the group consisting of docetaxel, etoposide, irinotecan, paclitaxel, teniposide, topotecan, vinblastine, vincristine and vinorelbine.

Another embodiment of the present invention comprises using a compound of formula 1 or any compound or formula disclosed herein with at least one agent selected from the group consisting of troxacitabine, altretamine, amifostine, asparaginase-*escherichia coli*, BCG live, cladribine, gemcitabine, leucovorin, levamisole, mitoxantrone, pegaspargase, pentostatin and procarbazine.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

One embodiment of the present invention also provides compositions which comprise a pharmaceutically acceptable carrier or adjuvant and an effective amount of a compound of formula 1, 2 or 3 to inhibit angiogenesis and/or tumor growth in a mammal. The proportion of each carrier, diluent or adjuvant is determined by the solubility and chemical nature of the compound and the route of administration according to standard pharmaceutical practice.

The individual components of such combinations may be administered either sequentially or simultaneously in separate or combined pharmaceutical formulations.

When the compound of formula 1 or any compound or formula disclosed herein is used in combination with a second therapeutic agent, the dose of each compound may be either the same as or differ from that when the compound is used alone. Appropriate doses will be readily appreciated by those skilled in the art.

Therapeutic and prophylactic methods of this embodiment of the invention comprise the step of treating patients in a pharmaceutically acceptable manner with those compounds or compositions. Such compositions may be in the form of tablets, capsules, caplets, powders, transdermal patches, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional excipients. For example, binding agents, such as acacia, gelatin, sorbitol, or polyvinylpyrrolidone; fillers, such as lactose, sugar, maize-starch, calcium phosphate, sorbitol or glycine; tableting lubricants such as magnesium stearate; disintegrants, such as starch, polyvinylpyrrolidone, sodium starch glycollate or microcrystalline cellulose; or pharmaceutically acceptable wetting agents such as sodium lauryl sulphate.

The compounds may be injected parenterally; this being intramuscularly, intravenously, or subcutaneously. For parenteral administration, the compound may be used in the form of sterile solutions containing other solutes, for example, sufficient saline or glucose to make the solution isotonic. The amount of active ingredient administered parenterally will be approximately 0.01 to 250 mg/kg/day, preferably about 1 to 10 mg/kg/day, more preferably about 0.5 to 30 mg/kg/day, and more most preferably about 1–20 mg/kg/day.

The compounds may be administered orally in the form of tablets, capsules, or granules containing suitable excipients such as starch, lactose, white sugar and the like. The compounds may be administered orally in the form of solutions which may contain coloring and/or flavoring agents. The compounds may also be administered sublingually in the form of tracheas or lozenges in which each active ingredient is mixed with sugar or corn syrups, flavoring agents and dyes, and then dehydrated sufficiently to make the mixture suitable for pressing into solid form. The amount of active ingredient administered orally will depend on bioavailability of the specific compound.

The solid oral compositions may be prepared by conventional methods of blending, filling, tableting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acaci; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl parahydroxybenzoate, ethyl parahydroxybenzoate, n-propyl parahydroxybenzoate, or n-butyl parahydroxybenzoate of sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. Once in solution, the compound may be injected and filter sterilized before filling a suitable vial or ampoule and subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying the composition). Parenteral suspensions may be prepared in substantially the same manner, except that the compound should be suspended in the vehicle rather than being dissolved, and, further, sterilization is not achievable by filtration. The compound may be sterilized, however, by exposing it to ethylene oxide before suspending it in the sterile vehicle. A surfactant or wetting solution may be advantageously included in the composition to facilitate uniform distribution of the compound.

The pharmaceutical composition of this invention comprise a compound of formula 1, 2 or 3 and a pharmaceutically acceptable carrier, diluent or adjuvant. Typically, they contain from about 0.1% to about 99% by weight of active compound, and preferably from about 10% to about 60% by weight depending on which method of administration is employed.

A pharmaceutically effective amount of compounds of the invention can be determined according to one or more of the assays described in detail in the examples. Under these particular conditions, a compound having such activity will exhibit an $IC_{50}$ of approximately 50 μg/ml or less, preferably 25 μg/ml or less, more preferably 10 μg/ml or less, and most preferably less than 1 μg/ml Physicians will determine the dosage of the present therapeutic agents which will be most suitable. Dosages may vary with the mode of administration and the particular compound chosen. In addition, the dosage may vary with the particular patient under treatment. The dosage of the compound used in the treatment will vary, depending on many factors including the weight of the patient, the relative efficacy of the compound and the judgment of the treating physician. Such therapy may extend for several weeks or months, in an intermittent or uninterrupted manner.

To further assist in understanding the present invention, the following non-limiting examples are provided.

EXAMPLE 1

Synthesis of the Compounds

Compound I: (2'S)5-(2'-Benzenesulfonylamino-2'-tert-butoxy carbonyl-ethylcarbamoyl)-thiophene-2-carboxylic acid.

Referring now to Scheme F herein, 2,5 thiophene dicarboxylic acid (200 mg, 1.16 mmol) was dissolved in 2 ml of anhydrous DMF and to this solution was added (2S)3-Amino-2-benzenesulfonylamino-propionic acid- tert-butyl ester (243 mg, 0.58 mmol), HATU (244 mg, 0.80 mmol) and 2,4,6-collidine (0.5 ml, 4.1 mmol). This reaction mixture was then left stirring at room temperature for two days. The solvent was evaporated under reduced pressure, the resulting residue was chromatographed on silica gel using first 10% acetone in dichloromethane, then 20% acetone in dichloromethane to clear out the impurities and the desired product was flushed out using a 50—50 acetone dichloromethane mixture. Evaporation of the desired fraction gave 200 mg of a white powder (Compound I). $^1$H NMR (400 MHz, DMSO-d6) 1.12 (s, 9H), 3.3 (m, 1H), 3.4 (m, 1H), 4.0 (q, 1H), 7.55 (m, 3H), 7.6 (d, 1H), 7.7 (d, 1H), 7.75 (d, 2H), 8.4 (d, 1H), 8.8 (t, 1H).

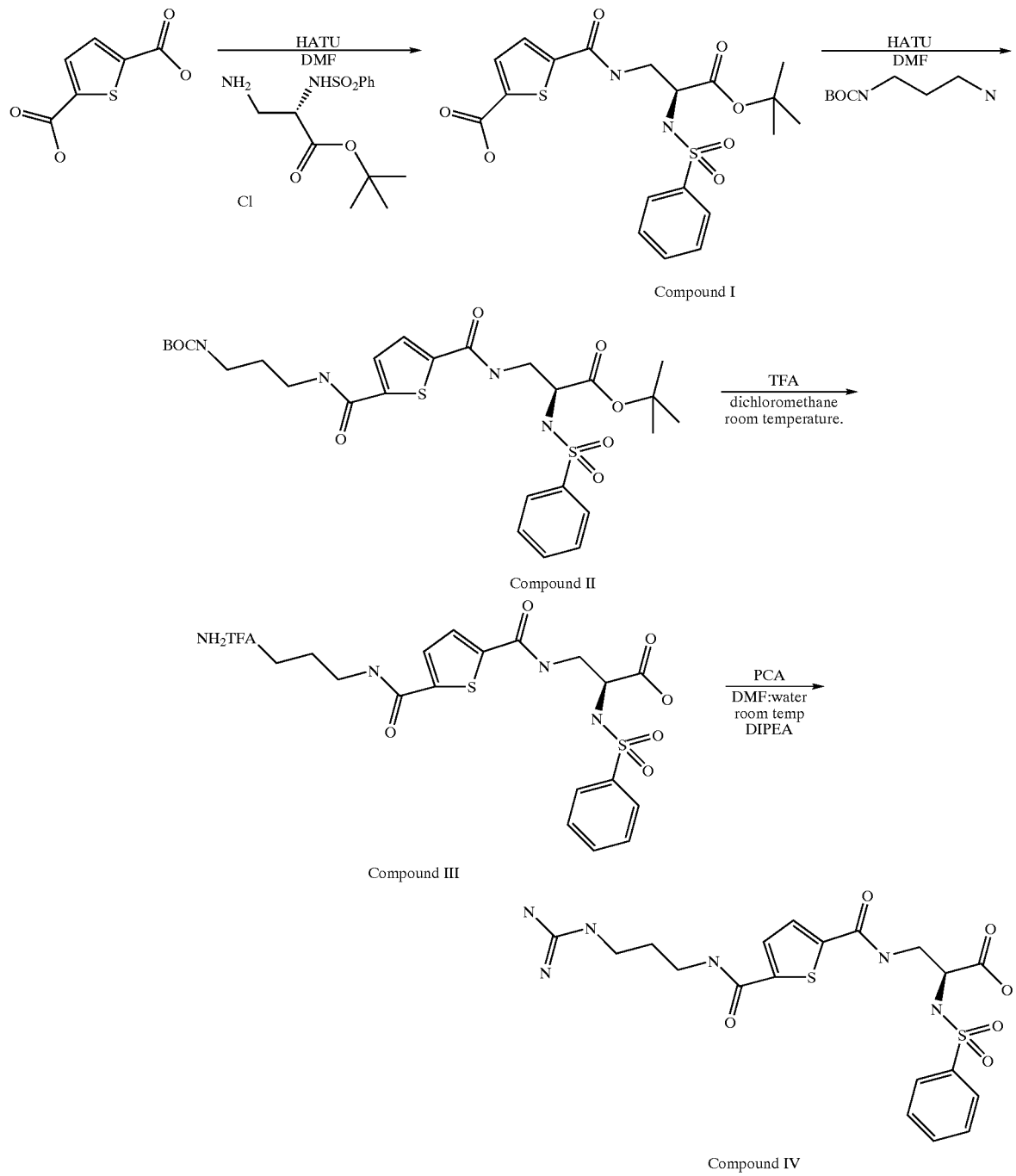

Compound II: 2-Benzenesulfonylamino-3-{[5-(3-tert-butoxycarbonylamino-propylcarbamoyl)-thiophene-2-carbonyl]-amino}-propionic acid-tert-butyl ester.

With continued reference to Scheme F, Compound I: (2'S)5-(2'-Benzenesulfonylamino-2'-tert-butoxycarbonyl-ethylcarbamoyl)-thiophene-2-carboxylic acid (200 mg, 0.47 mmol) was dissolved in 2 ml of anhydrous DMF and to this solution was added 1-N-Boc-1,3-diaminopropane (110 mg, 0.71 mmol), HATU (231 mg, 0.61 mmol) and 2,4,6-collidine (0.5 ml, 4.1 mmol). This reaction mixture was then left stirring at room temperature for 24 hrs. A large amount of ethyl acetate was added to the reaction mixture which was then washed successively with a 10% citric acid aqueous solution, a sodium bicarbonate solution and then brine. After separation the organic phase was dried over anhydrous MgSO$_4$ then filtrated on a pad of silica gel and the solvents were removed under reduced pressure to give 180 mg of a white powder (Compound II). $^1$H NMR (400 MHz, CDCl3) 1.3 (s, 9H), 1.5 (s, 9H), 1.7 (m, 2H), 3.3 (m, 2H) 3.5 (m, 2H), 3.55 (m, 1H), 3.9 (m, 2H), 4.85 (m, 1H), 5.65 (m, 1H), 6.7 (m, 1H), 7.45 (m, 1H), 7.55 (m, 4H), 7.6 (m, 1H), 7.9 (d, 2H).

Compound III: 2-Benzenesulfonylamino-3-{[5-(3-amino-propylcarbamoyl)-thiophene-2-carbonyl]-amino}-propionic acid, trifluoracetic acid salt.

With continued reference to Scheme F, Compound II: 2-Benzene-sulfonylamino-3-{[5-(3-tert-butoxycarbonylamino-propylcarbamoyl)-thiophene-2-carbonyl]-amino}-propionic acid-tert-butyl ester (180 mg, 0.95 mmol) was dissolved in 10 ml dichloromethane and 4.5 ml of anhydrous TFA. This reaction mixture was then left stirring over night at room temperature. The solvents were then removed under reduced pressure and the residue was dissolved in a small amount of methanol, then ether was added and the desired product precipitated out of the solution, the liquid was discarded and the residue was dried under vacuum to give a white powder (160 mg, 95%) (Compound III). $^1$H NMR (400 MHz, DMSO) 1.8 (m, 2H), 2.8 (m, 2H), 3.3 (m, 3H), 3.5 (m, 1H), 3.9 (m, 1H), 7.45 (m, 2H), 7.55 (m, 1H), 7.6 (d, 1H), 7.7 (d, 1H), 7.75 (bs, 4H), 7.75 (d, 2H), 8.6 (m, 1H), 8.75 (m, 1H).

Compound IV: 2-Benzenesulfonylamino-3-{[5-(3-guanidino-propylcarbamoyl)-thiophene-2-carbonyl]-amino}-propionic acid, trifluoracetic acid salt.

With continued reference to Scheme F. Compound III: 2-Benzenesulfonyl amino-3-{[5-(3-amino-propylcarbamoyl)-thiophene-2-carbonyl]-amino}-propionic acid, trifluoracetic acid salt (70 mg, 0.123 mmol) was dissolved in 2.0 ml distilled water containing 2.5 ml DMF with PCA (36 mg, 0.246 mmol) and DIPEA (158 mg, 1.23 mmol). This reaction mixture was heated until dissolution of the reagents then left to react over night at room temperature. The reaction mixture was concentrated under reduced pressure then chromatographed on silica gel using ethanol then 10% ammonium hydroxide in ethanol to elute starting materials then 20% ammonium hydroxide in ethanol to elute the desired product. Evaporation of the desired fraction gave 10 mg of a white powder (Compound IV). $^1$H NMR (400 MHz, DMSO) 1.65 (m, 2H), 3.1 (m, 2H), 3.2 (m, 2H), 3.4 (2H), 3.5 (m, 1H), 7–7.4 (bm, 5H), 7.5 (m, 4H), 7.65 (d, 1H), 7.8 (d, 2H), 8.2 (m, 1H), 8.55 (m, 1H), 8.75 (m, 1H).

SCHEME G

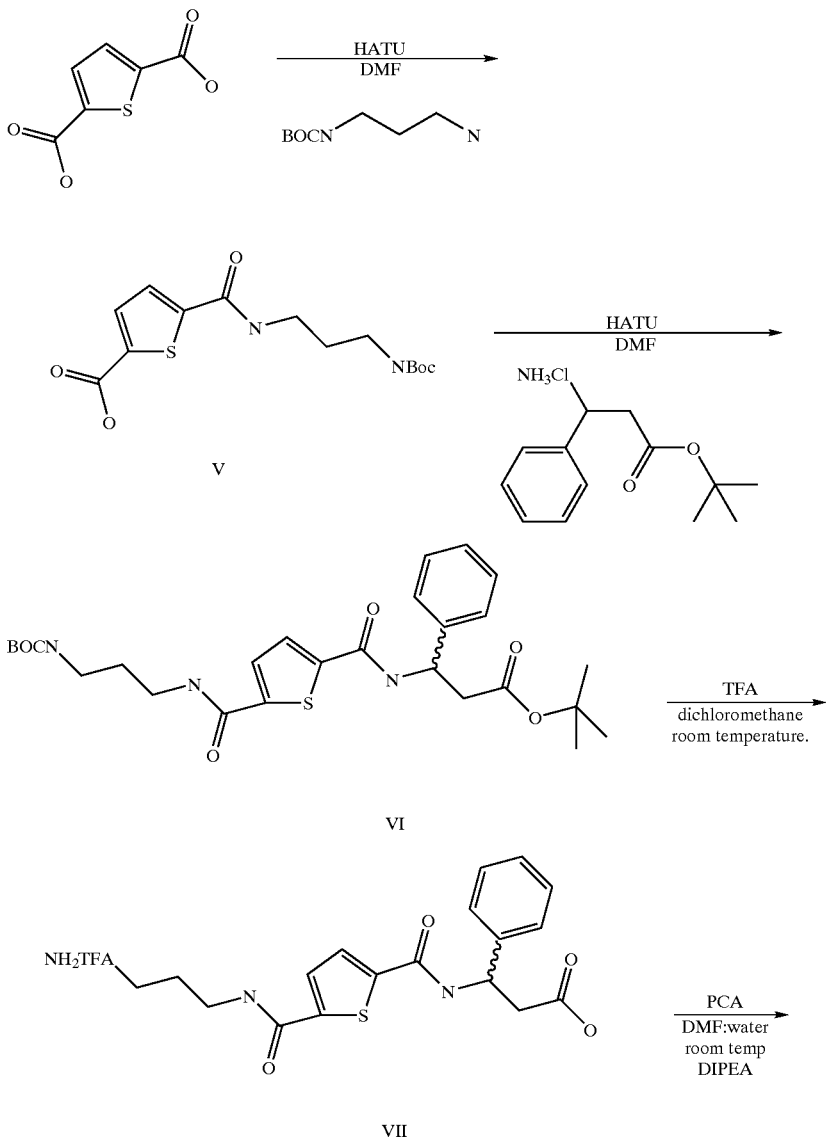

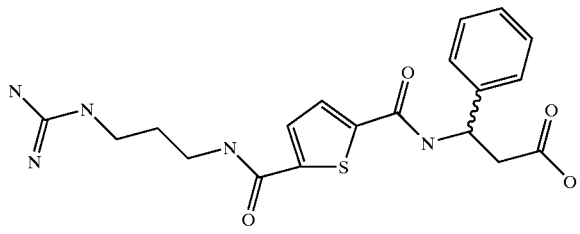

VIII

Compound V: 5-(3-tert-Butoxycarbonylamino-propylcarbamoyl)-thiophene-2-carboxylic acid.

Referring now to Scheme G herein, 2,5-thiophene dicarboxylic acid (1 g, 5.8 mmol) was reacted with N-Boc-1,3-diaminopropane (0.9 g, 5.8 mmol) in 20 ml of anhydrous DMF using HATU (2.2 g, 5.8 mmol) with 2,4,6-collidine (2.5 ml, 5.8 mmol), chromatographied on silica gel using ethyl acetate: methanol (9:1) to give 350 mg (18% yield) of the desired product (Compound V) contaminated with the product of bis addition. $^1$H NMR (400 MHz, DMSO-d6) 1.3 (s, 9H), 1.6 (m, 2H), 2.95 (m, 2H), 3.2 (m, 2H), 7.7 (m, 2H), 8.6 (t, 1H).

Compound VI: 3-{[5-(3-tert-Butoxycarbonylamino-propylcarbamoyl)-thiophene-2-carbonyl]-amino}-3-phenyl-propionic acid tert-butyl ester.

With continued reference to Scheme G, 5-(3-tert-Butoxycarbonylamino-propylcarbamoyl)-thiophene-2-carboxylic acid (200 mg, 0.704 mmol) was reacted with 3-Amino-3-phenyl-propionic acid tert-butyl ester (187 mg, 0.845 mmol) in 4.0 ml of anhydrous DMF using HATU (321 mg, 0.845 mmol) with 2,4,6-collidine (0.25 ml, 2.112 mmol), chromatographied on silica gel using ethyl acetate: hexane (8:2) to give 200 mg (58% yield) of the desired product as a clear semi-solid oil. $^1$H NMR (400 Mhz, CDCl$_3$) 1.3 (s, 9H), 1.45 (s, 9H), 1.7 (m, 2H), 2.9 (ddd, 2H), 3.25 (m, 2H), 3.5 (q, 2H), 4.85 (bs, 1H), 5.55 (m, 1H), 7.23 (m, 1H), 7.33 (m, 4H), 7.4–7.6 (m, 4H).

Compound VII: 3-{[5-(3-Amino-propylcarbamoyl)-thiophene-2-carbonyl]-amino}-3-phenyl-propionic acid trifluoroacetic acid salt.

With continued reference to Scheme G, preparation of compound VII was carried out using the procedure described for compound III. Compound VI: 3-{[5-(3-tert-Butoxycarbonylamino-propylcarbamoyl)-thiophene-2-carbonyl]-amino}-3-phenyl-propionic acid tert-butyl ester (200 mg, 0.704 mmol) was dissolved in 4.0 ml of anhydrous dichloromethane and 4.0 ml of anhydrous TFA. This reaction mixture was left stirring over night at room temperature. The solvents were evaporated under reduced pressure and the resulting residue was dissolved in anhydrous methanol (smallest amount possible). Diethyl ether was then added to precipitate the desired product, the supernatant was discarded and the solid washed with ether again then dried under reduced pressure to give 156 mg of the desired product as a white powder (Compound VII). $^1$H NMR (400 Mhz, DMSO-d6) 1.75 (m, 2H), 2.9 (m, 4H), 3.3 (m, 2H), 7.2–7.4 (m, 5H), 7.4 7.9 (bs, 3H), 7.65 (d, 1H), 7.8 (d, 1H), 8.75 (t, 1H), 9.05 (d, 1H).

Compound VIII: 3-{[5 (3-guanidino-propylcarbamoyl)-thiophene-2-carbonyl]-amino}-3-phenyl-propionic acid.

With continued reference to Scheme G. Compound VII: 3-{[5-(3-Amino-propylcarbamoyl)-thiophene-2-carbonyl]-amino}-3-phenyl-propionic acid (50 mg, 0.102 mmol) was dissolved 1.0 ml in anhydrous DMF with PCA (30 mg, 0.204 mmol) and DIPEA (0.3 ml, 1 mmol). This reaction mixture was heated at 60–70° C. for 4 hours. The reaction mixture was concentrated under reduced pressure then chromatographed on silica gel using ethanol then 10% ammonium hydroxide in ethanol to elute starting materials then 40% ammonium hydroxide in ethanol to elute the desired product. Evaporation of the desired fraction gave 21 mg (50% yield) of a white powder. Compound VIII $^1$H NMR (400 MHz, DMSO) 1.7 (m, 2H), 2.7 (m, 1H), 3.1 (m, 2H), 3.25 (m, 2H), 5.25 (m, 1H), 7.2–7.4 (m, 5H), 7.6 (bs, 4H), 7.7 (d, 1H), 7.75 (d, 1H), 8.8 (s,1H), 8.9 (s, 1H), 9.65 (s, 1H).

SCHEME H

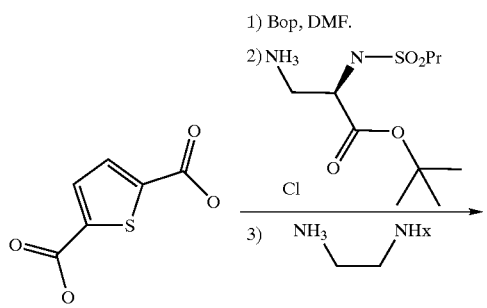

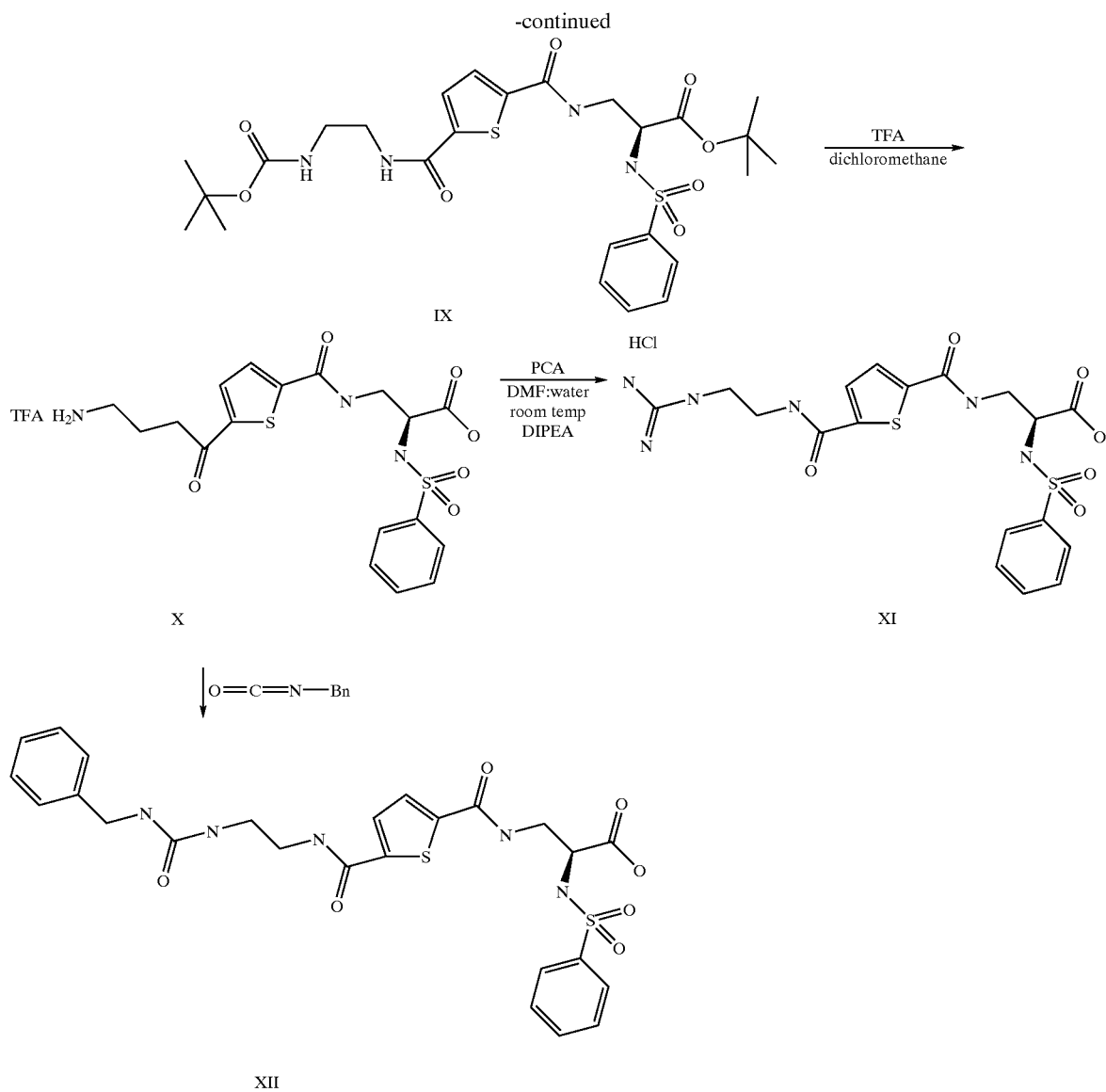

XII

Compound IX: (2S)2-Benzenesulfonylamino-3-{[5-(2-tert-butoxycarbonylamino-ethylcarbamoyl)-thiophen-2-carbonyl]-amino propionic acid tert-butyl ester.

Referring now to Scheme H, benzotriazole-1-yl-oxy-tris(dimethylamino)-phosphonium hexafluorophosphate (Bop reagent) (514 mg, 1.162 mmol) as added, in one portion, to a mixture of 2,5-thiophene dicarboxylic acid (100 mg, 0.581 mmol). The mixture was stirred for 20 min. and a solution of the 3-tert-butylcarbonylaminoethylamine (93 mg, 0.581 mmol) in 1 ml of the same solvent, was added one drop at a time. This mixture was stirred for 6 hours. A solution of 2-benzenesulfonylamino-3-amino-propionic acid tert-butylester hydrochloride (196 mg, 0.581 mmol) and dimethylaminopyridine (355 mg, 2.905 mmol) in 1 ml of the same solvent was added dropwise. The mixture was stirred overnight, concentrated (to eliminate the DMF), diluted in ethyl acetate, washed with KHSO4 10%, NaHCO3 sat. , brine and dried (anhydrous $MgSO_4$). Flash chromatography using dichloromethane:acetone(85:15) gave 157 mg of the pure desired product (Compound IX: 45% yield). $^1$H NMR (400 MHz, CD3OD) 1.24 (s, 9H), 1.42 (s, 9H), 3.25–3.28 (m, 2H), 3.42–3.45 (m, 2H), 3.46–3.52 (dd, 1H), 3.63–3.69 (dd, 1H), 4.10–4.14 (dd, 1H), 7.47–7.51 (m, 2H), 7.53–7.57 (m, 3H), 7.60–7.61 (m, 2H), 7.83–7.85 (m, 2H).

Compound X: (2S)2-Benzenesulfonylamino-3-[5-(2-aminoethylcarbamoyl)-thiophen-2-carbonyl]-amino propionic acid trifluoroacetic acid salt.

With continued reference to Scheme H, TFA (1.5) ml was added to a mixture of Compound IX: (2S)2-Benzenesulfonylamino-3-{[5-(2-tert-butoxycarbonylamino-ethylcarbamoyl)-thiophen-2-carbonyl]-amino propionic acid tert-butyl ester (151 mg, 0.253 mmol) in anhydrous dichloromethane (1.5 ml). The mixture was stirred 1 hour (and was followed on TLC) then concentrated. The crude oil residue was triturated in ether and filtrated to give the deprotected amino acid (white solid) as a TFA salt which was used in the next experiment without further purification (Compound X). $^1$H NMR (400 MHz, CD3OD) 3.14–3.18 (m, 2H), 3.45–3.51 (m, 1H), 3.63–3.67 (m, 2H), 3.71–3.76 (dd, 1H), 4.17–4.21 (dd, 1H), 7.43–7.54 (m, 3H), 7.58 (d, 1H), 7.64 (d, 1H), 7.83–7.85 (dd, 1H).

Compound XI: (2S)2-Benzenesulfonylamino-3-[5-(2-guanidinyl-ethylcarbamoyl)-thiophen-2-carbonyl]-amino propionic acid hydrochloride salt.

'With continued reference to Scheme H, Compound X: (2S)2-Benzenesulfonylamino-3-[5-(2-amino-ethylcarbamoyl)-thiophen-2-carbonyl]-amino propionic acid TFA salt was dissolved in 1.25 ml of water and 1.25 ml of DMF. DIPEA (132 ul, 0.759 mmol) and PCA (56 mg, 0.380 mmol) were added successively. The mixture was stirred at 60° C. for 6 hours, cooled down to room temperature (room temperature) and concentrated. Flash chromatography ethanol: ammonium hydroxide:water (8:1:1) gave the guanidinyl compound which was lyophilized in a HCl 0.05 N in water to give 95 mg of the desired compound as a hydrochloride salt. $^1$H NMR (400 MHz, CD3OD) 3.43–3.46 (m, 2H), 3.47–3.51 (m, 1H), 3.54–3.55 (m, 2H), 3.71–3.75 (dd, 1H), 4.18–4.20 (dd, 1H), 7.43–7.51 (m, 3H), 7.57 (bm, 1H), 7.64 (bm, 1H), 7.83 (m, 2H).

Compound XII: (2S)2-Benzenesulfonylamino-3-(5-[2-(3-benzyl-ureido)-ethylcarbamoyl]-thiophen-2-carbonyl-amino) propionic acid.

With continued reference to Scheme H, to a mixture of Compound X: (2S)2-Benzenesulfonylamino-3-[5-(2-amino-ethylcarbamoyl)-thiophen-2-carbonyl]-amino) propionic acid TFA salt (23 mg, 0.042 mmol) in acetonitrile (0.25 ml) and anhydrous DMF (0.25 ml) was added triethylamine (11.7 uL, 0.084 mmol) and benzyl isocyanate (5.3 uL, 0.042 mmol). The mixture was stirred for 20 min. An additional portion of benzyl isocyanate (2.5 uL) was added. After 1 hour of stirring, the mixture was diluted with ethyl acetate, washed with HCl 0.1 N and dried ($Na_2SO_4$). Filtration of the crude through silica mega bound elute system methanol dichloromethane (4:6) and evaporation of the desired fractions gave a white powder (Compound XII). $^1$H NMR (300 MHz, D2O) 3.15–3.25 (m, 3H), 3.30–3.33 (m, 2H), 3.49–3.55 (dd, J=14.5 and 3.5 Hz, 1H), 3.75–3.80 (dd, J=10.5 and 4.0 Hz, 1H), 4.09 (s, 2H), 7.04–7.08 (m, 5H), 7.12–7.13 (m, 4H), 7.29 (d, J=4.0 Hz, 1H), 7.54–7.58 (m, 2H).

Scheme I

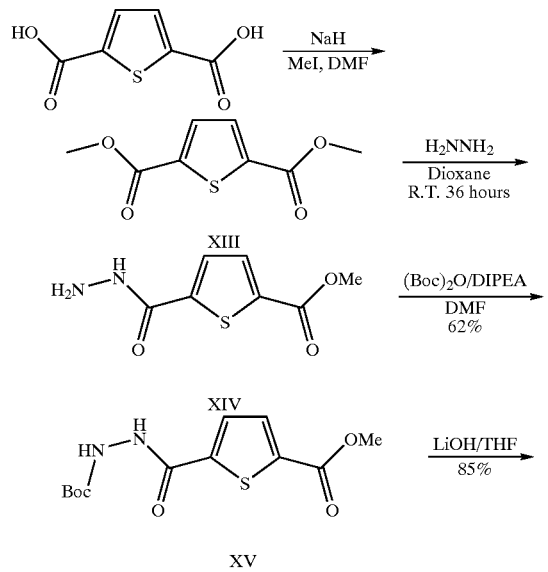

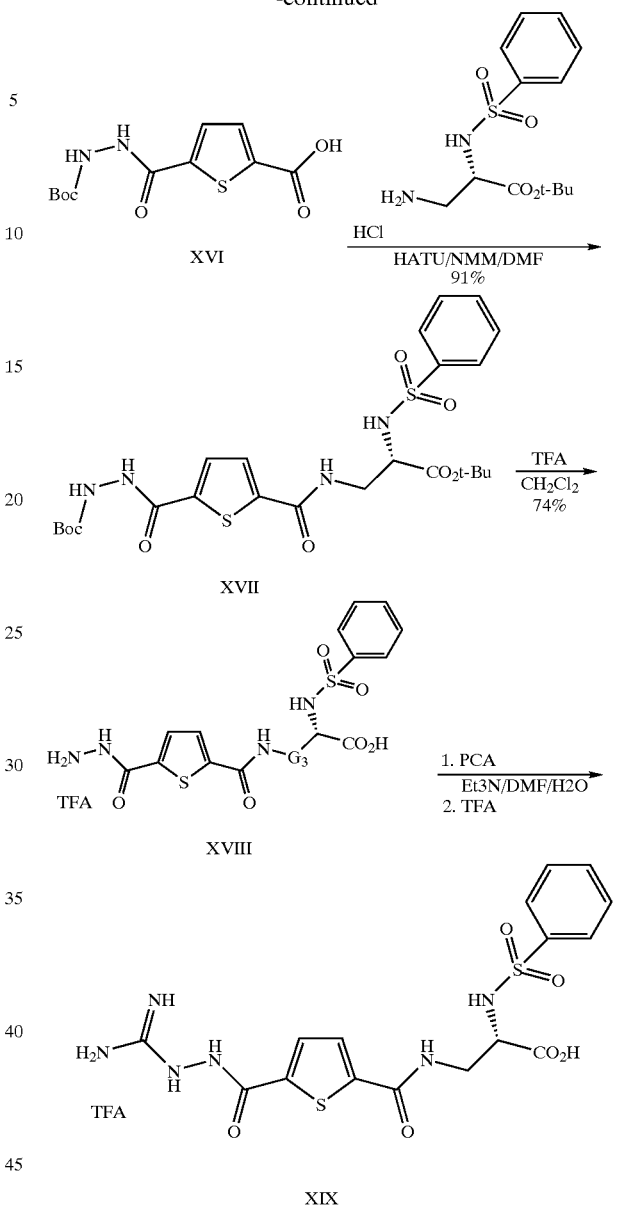

Compound XIII: Dimethyl-2,5-thiophenedicarboxylic Diester.

Now referring to Scheme I, sodium hydride, 60% in oil, (1.9 g, 0.046 mol) was added to a stirring solution of 2,5-thiophenedicarboxylic acid (4.0 g, 0.023 mol) in anhydrous DMF (40 ml). This reaction mixture was left stirring at room temperature for an additional 10 min. Then iodomethane (6.0 ml) was added and the resulting suspension was stirred 24 hrs at room temperature. The solvent was evaporated under reduced pressure and the residue was extracted with a mixture of ethylacetate: distilled water and the organic layer was separated and the solvent was evaporated under reduced pressure, the residue was triturated with hexane (diethyl ether can also be used), then dried under vacuum leaving (4 g, 86%) of a pale yellow powder Compound XIII: $^1$H NMR (300 MHz, CDCl$_3$) 3 3.92 (s, 6H), 7.73 (s, 2H).

Compound XIV: 5-hydrazinocarbonyl-thiophene-2-carboxylic acid methyl ester.

With continued reference to Scheme I, Compound XIII: Dimethyl-2,5-thiophenedicarboxylic diester (600 mg, 3 mmol) was dissolved in 20 ml of anhydrous dioxane and hydrazine (192 mg, 6 mmol). This solution was stirred at room temperature for 7 days. During this period of time a precipitate formed at the bottom of the flask. This precipitate was filtrated then dried under reduced pressure to give a white powder Compound XIV (200 mg, 33%). $^1$H NMR (300 MHz, DMSO) 3.8 (s, 3H), 7.7 (d, 1H), 7.8 (d, 1H), 9.9 (s, 1H), 10.1 (s, 1H).

Compound XV: 5-(N'-tert-Butoxycarbonyl-hydrazinocarbonyl)-thiophene-2-carboxylic acid methyl ester.

With continued reference to Scheme I, di tert-butyl dicarbonate (188 mg, 0.861 mmol) and DIPEA (170 µl, 0.976 mmol) were sequentially added to a stirring mixture of Compound 5-Hydrazinocarbonyl-thiophene-2-carboxylic acid methyl ester (115 mg, 0.575 mmol) in anhydrous DMF (2.0 ml) at 0° C. The resulting mixture was allowed to stir at room temperature overnight. The solvent was removed under vacuum and the resulting residue subjected to a silica gel chromatography using Hexane: EtOAc (1:1) to give the desired product as a white solid (107.7 mg, 62.4%) $^1$H NMR in DMSO-$d_6$ 1.42 (s, 9H), 3.84 (s, 3H), 7.72–7.88 (m, 2H), 9.06 (bs, 1H), 10.5 (bs, 1H);

Compound XVI: 5-(N-tert-Butoxycarbonyl-hydrazinocarbonyl)-thiophene-2-carboxylic acid.

With continued reference to Scheme I, a 2 mL aqueous LiOH solution (35.7 mg, 85 mmol, lithium hydroxide monohydrate in 2 mL H$_2$O) was added to a stirring solution of Compound XV: 5-(N' tert-Butoxycarbonyl-hydrazinocarbonyl)-thiophene-2-carboxylic acid methyl ester (85 mg, 0.28 mmol) in THF (4 ml) at room temperature. The mixture was stirred at room temperature overnight. The organic solvent was evaporated and the mixture acidified with HCl (1M solution in ether) to pH=5. The desired acid (Compound XCVI) was collected by filtration and used in the next step without further purification (70 mg, 86%). $^1$H NMR CD$_3$OD 1.42 (s, 9H), 7.86–7.79 (m, 2H), 9.06 (bs, 1H), 10.43 (bs, 1H).

Compound XVII: 2S-Benzenesulfonylamino-3-{[5-(N-tert-Butoxycarbonyl-hydrazinocarbonyl)-thiophene-2-carbonyl]-amino}-propionic acid tert-butyl ester.

With continued reference to Scheme I, 3-amino-2S-benzenesulfonylamino-propionic acid tert-butyl ester hydrochloride (64.7 mg, 0.192 mmol), NMM (57.7 µl, 0.525 mmol) and HATU (76.4 mg, 2.01 mmol) were sequentially added to a stirring mixture of 5-(N'-tert-Butoxycarbonyl-hydrazinocarbonyl)-thiophene-2-carboxylic acid (50 mg, 0.175 mmol) in anhydrous DMF (5.2 ml) at room temperature. The resulting mixture was allowed to stir at room temperature for 2 hrs. The solvent was removed under vacuum and the resulting residue subjected to a silica gel chromatography EtOAc: Hexane (1.5:0.5) to give the desired product (Compound XVII) as a white solid (90 mg, 91%): $^1$H NMR in CDCl$_3$ 1.29 (s, 9H), 1.48 (s, 9H), 3.70–3.85 (m, 3H), 4.05 (m, 1H), 6.38 (bs, 1H), 7.18 (bs, 1H), 7.35–7.90 (m, 7H), 9.44 (bs, 1H);

Compound XVIII: 2S-Benzenesulfonylamino-3-[(5-hydrazinocarbonyl-thiophene-2-carbonyl)-amino]-3-propionic acid trifluoroacetate.

With continued reference to Scheme I, TFA (0.6 ml) was added to a stirred solution of Compound XVII: 2S-Benzenesulfonylamino-3-{[5-(N'-tert-Butoxycarbonyl-hydrazinocarbonyl)-thiophene-2-carbonyl]-amino-propionic acid tert-butyl ester (10 mg, 0.0176 mmol) in dichloromethane (0.6 ml) at room temperature. The resulting mixture was stirred at room temperature for 45 min. The solvent was removed under vacuum and the resulting residue was triturated from MeOH-Et2O to give the desired product (compound XVIII) (6.8 mg, 74%) m.p. 185° C. (dec), $^1$H NMR in DMSO-$d_6$ 3.45–3.55 (m, 1H), 4.0 (dd, 1H), 7.4–7.55 (m, 3H), 7.57 (d, 1H), 7.64 (d, 1H), 7.70–7.78 (m, 2H), 8.24 (d, 1H), 8.62, (t, 1H), 10.06 (bs, 1H); m/z 413 M$^+$.

Compound XIX: 2S-Benzenesulfonylamino-3-[(5-guanidino-aminocarbonyl-thiophene-2-carbonyl)-amino]-3-propionic acid trifluoroacetate.

With continued reference to Scheme I, TFA (1.2 ml) was added to a stirred solution of Compound XVIII: 2S-Benzenesulfonylamino-3-{[5-(N'-tert-Butoxycarbonyl-hydrazinocarbonyl)-thiophene-2-carbonyl]-amino{-propionic acid tert-butyl ester (30 mg, 0.053 mmol) in dichloromethane (1.2 ml) at room temperature. The resulting mixture was stirred at room temperature for 45 min. The solvent was removed under vacuum and the resulting residue was redissolved in DMF-H$_2$O (0.4 ml/0.4 ml). PCA (15.48 mg, 0.106 mmol) and DIPEA (73.6 µl, 0.423 mmol) were added. The resulting mixture was heated at 60° C. for 4 hours and then the solvent was evaporated to yield a solid residue. Chromatography of the crude EtOH: H2O: NH$_4$OH (1.8:0.1:0.1) gave the desired product which was lyopholized to afford the product as a white solid (13 mg, 54%. Part of the product was mixed with dichloromethane (5 ml), a few drops of methyl alcohol and TFA. The mixture was turn clear and the solvent was evaporated to a white solid which was further triturated from MeOH-Et2O to afford purer product (Compound XIX); 205° C. (dec). $^1$H NMR in CD3OD 3.73 (dd, 1H), 4.19 (dd, 1H), 3.46 (dd, 1H), 7.40–7.55 (m, 3H), 7.59 (d, 1H), 7.73 (d, 1H), 7.78–7.85 (m, 2H); m/z 455 M$^+$.

Compound XX: (S)-3-((S-(2-Amino-ethylcarbamoyl)-furan-2-carbonyl)-amino)-2-benzenesulfonylamino-propionic acid trifluoroacetate.

Compound XX

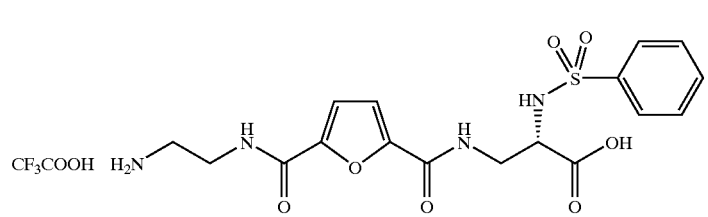

Compound XX was made using 2,5-furan dicarboxylic acid as the starting material. Otherwise, the same procedure was followed as illustrated in Scheme H for producing compound X. The resulting compound was obtained as a white powder: (HNMR, 400 MHz, CD$_3$OD) d: 7.85 (m, 2H), 7.35–7.55 (m, 3H), 7.17 (d, 1H), 7.12 (d, 1H), 4.07 (dd, 1H), 3.64–3.80 (m, 3H), 3.55 (dd, 1H), 3.19 (br, 2H).

Compound XXI: (s)-2-Benzenesulfonylamino-((5-(2-guanidino-ethylcarbamoyl)-furan-2-carbonyl)-amino)-propionic acid hydrochloride.

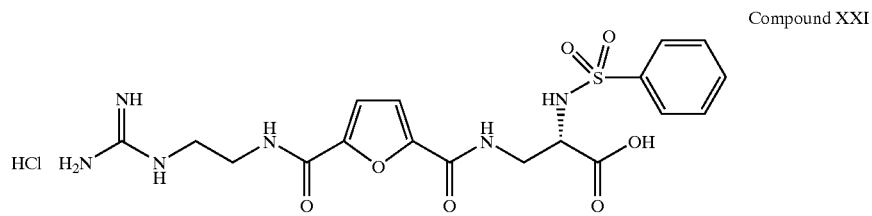

Compound XXI was made using 2,5 dicarboxilic acid as a starting material. Otherwise the same procedure was followed as illustrated in Scheme II for producing Compound XI. Compound XXI was obtained as a white lyophilized powder: (HNMR, 400 MHz, CD$_3$OD) d: 7.83 (m, 2H), 7.35–7.50 (m, 3H), 7.18 (d, 1H), 7.09 (d, 1H), 4.22 (dd, 1H), 3.78 (dd, 1H), 3.60 (m, 2H), 3.47 (m, 3H).

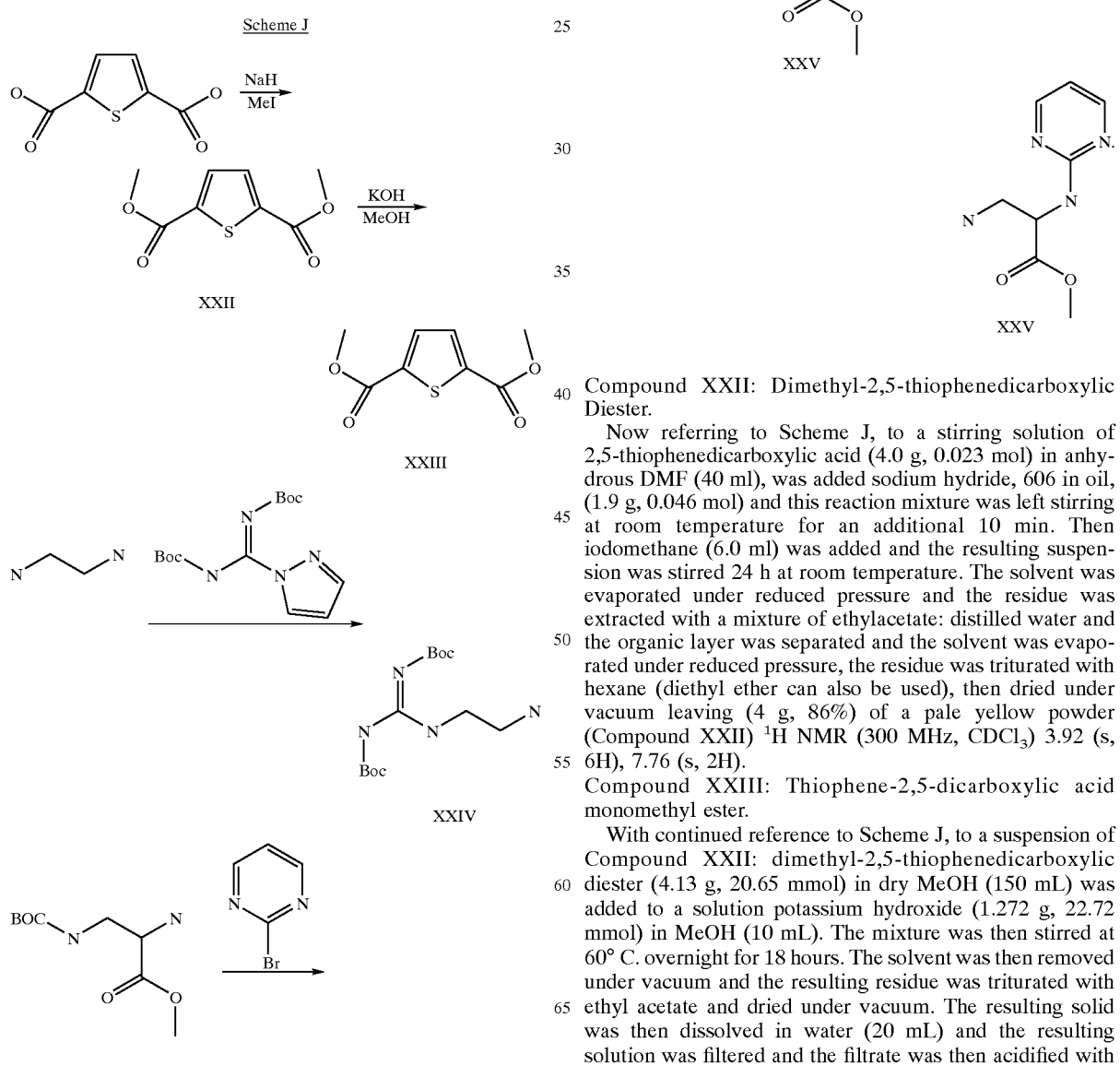

Compound XXII: Dimethyl-2,5-thiophenedicarboxylic Diester.

Now referring to Scheme J, to a stirring solution of 2,5-thiophenedicarboxylic acid (4.0 g, 0.023 mol) in anhydrous DMF (40 ml), was added sodium hydride, 606 in oil, (1.9 g, 0.046 mol) and this reaction mixture was left stirring at room temperature for an additional 10 min. Then iodomethane (6.0 ml) was added and the resulting suspension was stirred 24 h at room temperature. The solvent was evaporated under reduced pressure and the residue was extracted with a mixture of ethylacetate: distilled water and the organic layer was separated and the solvent was evaporated under reduced pressure, the residue was triturated with hexane (diethyl ether can also be used), then dried under vacuum leaving (4 g, 86%) of a pale yellow powder (Compound XXII) $^1$H NMR (300 MHz, CDCl$_3$) 3.92 (s, 6H), 7.76 (s, 2H).

Compound XXIII: Thiophene-2,5-dicarboxylic acid monomethyl ester.

With continued reference to Scheme J, to a suspension of Compound XXII: dimethyl-2,5-thiophenedicarboxylic diester (4.13 g, 20.65 mmol) in dry MeOH (150 mL) was added to a solution potassium hydroxide (1.272 g, 22.72 mmol) in MeOH (10 mL). The mixture was then stirred at 60° C. overnight for 18 hours. The solvent was then removed under vacuum and the resulting residue was triturated with ethyl acetate and dried under vacuum. The resulting solid was then dissolved in water (20 mL) and the resulting solution was filtered and the filtrate was then acidified with HCl (1 N). The precipitate (Compound XXIII) was then collected by filtration and dried under vacuum (2.50 g, 65%). ¹H NMR (300 MHz, DMSO) δ: 13.73 (br s, 1 H), 7.79 (d, 1 H), 7.72 (d, 1 H), 3.85 (s, 3 H).

Compound XXIV: N,N'-Bis-(Boc)-N''-(2-Amino-ethyl)-guanidine.

With continued reference to Scheme J, a solution of the N,N'-bis-(Boc)-1H-Pyrazole-1-carboxamidine (2 g, 6.45 mmol) in THF (50 ml) was added dropwise to ethylene diamine (4 ml, 59.6 mmol) in THF (100 ml). After 30 min of mixing at room temperature solvent was evaporated then toluene (100 ml) was added and evaporated in order to remove remaining traces of the ethylene diamine. The resulting product (Compound XXIV) was treated immediately according to scheme K since it decomposes at room temperature. ¹H NMR (CDCl₃, 400 MHz) δ 1.40–1.61 (m, 18H), 2.87–2.90 (t, 2H,), 3.47–3.50 (m, 2H), 6.31–6.34 (t, 0.61H), 7.61–7.62 (d, 1H), 8.45–8.66 (broad s).

Compound XXV: 3-tert-Butoxycarbonylamino-2-(pyrimidin-2-ylamino)-propionic acid methyl ester.

With continued reference to Scheme J, methyl 2-amino-3(N-t-butyoxycarbonylamino)propionate (240 mg, 1.10 mmol), 2-bromopyrimidine (350 mg, 2.20 mmol) is obtained according to the disclosure found in Egbertson et al., Synthetic Communications, vol. 23, pp. 703 et seq. (1993) incorporated herein fully by reference. Methyl 2-amino-3-(N-E-butyoxy carbonyl amino) propionate was then mixed with and sodium carbonate (117 mg, 1.10 mmol) in DMF (1 mL). The resulting mixture was stirred at 100° C. for about 20 hours. The reaction mixture was concentrated under vacuum and the residue was purified by chromatography eluting with 50% ethyl acetate in hexane. The resulting product Compound XXV was obtained as a foam (174 mg, 53%) ¹H NMR (400 MHz, CDCl₃) δ:8.30 (d, 2 H), 6.61 (t, 1 H) 6.02 (br s, 1 H), 4.94 (br s, 1 H), 4.76 (br d, 1 H), 3.78 (s, 3 H), 3.67 (br s, 2 H), 1.43 (s, 9 H).

Compound XXVI: (3-Amino-2-(pyrimidin-2-ylamino)-propionic acid methyl ester bis hydrochloride salt.

With continued reference to Scheme J, a solution of Compound XXV: 3-tert-Butoxycarbonylamino-2-(pyrimidin-2-ylamino)-propionic acid methyl ester (227 mg, 0.77 mmol) in HCl/dioxane (4 N, 5 mL) was stirred at room temperature for 1 hour. The solution was then concentrated to dryness and the residue was dissolved in water (20 mL). This solution was then washed with dichloromethane (2×10 mL) and hexanes (10 mL). The solution was then filtered and lyophilized to a yellow solid (Compound XXVI: 185 mg, 90%) ¹H NMR (400 MHz, DMSO) δ:8.70 (d, 2 H), 8.20 (br s, 2 H), 7.69 (br d, 1 H), 6.75 (t, 1 H), 5.79 (br, 3 H), 4.80 (br d, 1 H), 3.78 (s, 3 H), 3.64 (br s, 2 H), 3.2 (br s, 2 H).

Scheme K

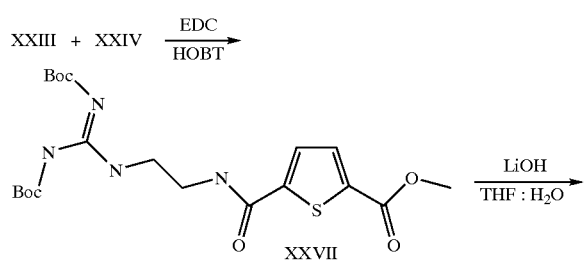

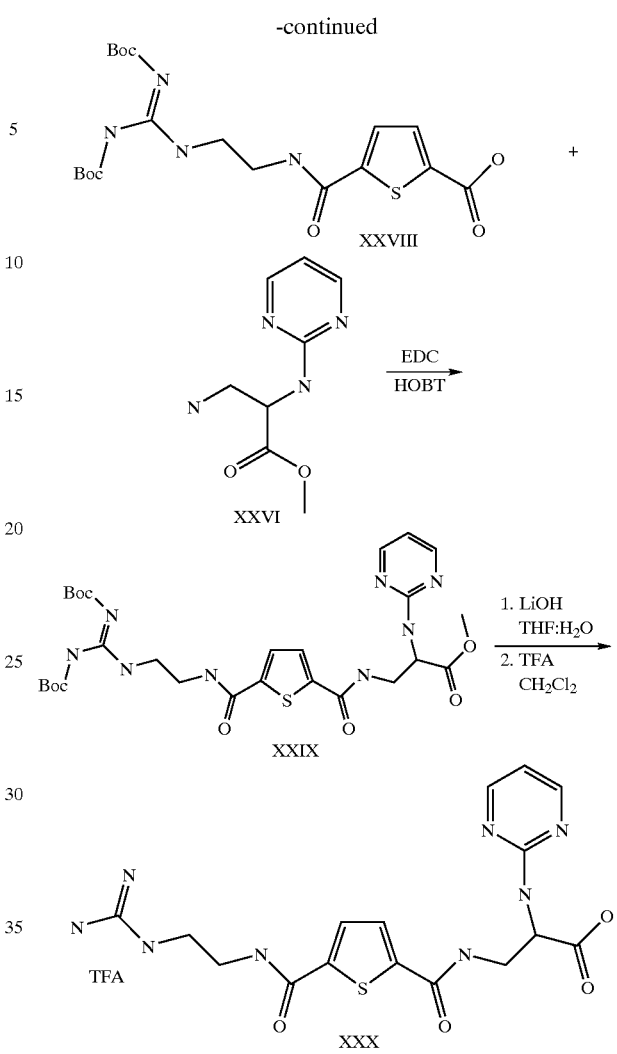

Compound XXVII: 5-(2-(N,N'-Bis-(BOC)-guanidino)-ethylcarbamoyl)-thiophene-2-carboxylic acid methyl ester.

Now referring to Scheme K, to Compound XXIII: thiophene-2,5-dicarboxylic acid monomethyl ester (923 mg, 4.96 mmol) in DMF (10 ml) was added 1-hydroxybenzotriazole (HOBT) (870 mg, 6.45 mmol) followed by 1-[3-(dimethylamino)propyl]-3-ethylcarbodiimide hydrocloride (EDC) (1.23 g, 6.45 mmol) and (1.2 ml, 10.9 mmol) of NMM. Compound XXIV: N,N'-Bis-(Boc)-N''-(2-Amino-ethyl)-guanidine (6.45 mmol, 1.96 g) was then added in DMF(10 ml) to the reaction mixture which was then left to stir at room temperature for 16 hours. Solvent was evaporated and the residue was thrown in a 10% citric acid solution (50 ml) and extracted with ETOAC (3×70 ml). The organic phases were combined and washed with a saturated solution of NaHCO₃ followed by a solution of Brine, dried over MgSO₄ and evaporated. The crude residue was then purified by flash column chromatography using CH₂Cl₂/MeOH (10:0.2) to give the desired product (Compound XXVII) in 94% yield. ¹H NMR (CDCl₃, 400 MHz) δ 1.1–1.34 (m, 21H), 3.41–3.81 (m, 4H), 3.88 (s, 3H), 5.58–5.59 (d, 1H), 7.69–7.70 (d, 1H), 8.43–8.54 (broad s, 1H), 8.70–8.88 (m, 1H).

Compound XXVIII: 5-(2-(N,N'-Bis-(BOC)-guanidino)-ethylcarbamoyl)-thiophene-2-carboxylic acid.

With continued reference to Scheme K, To Compound XXVII: 5-(2-(N,N'-Bis-(BOC)-guanidino)- ethylcarbamoyl)-thiophene-2-carboxylic acid methyl ester (2.2 g, 4.66 mmol) in 50% THF/H$_2$O (50 ml) was added 1.5 eq. of LiOH (294 mg, 6.99 mmol) and the reaction mixture was left to stir at room temperature for 3 hours. 10% citric acid solution was added until acidic pH and THF was evaporated. The aqueous solution was then extracted with CH$_2$Cl$_2$ (3×70 ml). The organic phases were combined and washed with a solution of Brine, dried over MgSO$_4$ and evaporated to give the desired product in 84% yield. $^1$H NMR (CD$_3$OD, 400 MHz) δ 1.34–1.66 (m, 21H), 3.49–3.67 (m, 4H), 7.61–7.70 (dd, 2H).

Compound XXXIX: 3-{[5-(2-(N,N'-Bis-(BOC)-guanidino)-ethylcarbamoyl)-thiophene-2-carbonyl]-amino}-2-(pyrimidin-2-ylamino)-propionic acid methyl ester.

With continued reference to Scheme K, a solution of Compound XXVIII: 5-(2-(N,N'-Bis-(BOC)-guanidino)-ethylcarbamoyl)-thiophene-2-carboxylic acid (100 mg, 0.22 mmol), Compound XXVI: (3-Amino-2-(pyrimidin-2-ylamino)-propionic acid methyl ester bis hydrochloride salt (64 mg, 0.24 mmol), EDC (46 mg, 0.24 mmol), HOBt (32 mg, 0.24 mmol) and N-methylmorpholine (96 µL, 0.88 mmol) in DMF (2 mL) was stirred at rt for 48 hrs. The solution was then concentrated to dryness and the residue was purified by chromatography eluting with 2–5% MeOH in dichloromethane. The resulting product (Compound XXIX) is obtained as a white solid (100 mg, 74%) $^1$H NMR (400 MHz, CDCl$_3$) δ:11.31 (s, 1 H), 8.92 (br s, 1 H), 8.56 (br s, 1 H), 8.36 (d, 2 H), 7.51 (d, 1 H), 7.43 (br s, 1 H), 6.68 (t, 1 H), 6.30 (br s, 1 H), 4.88 (m, 1 H), 4.05 (m, 1 H), 3.82 (s, 3 H), 3.76 (m, 2 H), 3.61 (m, 2 H), 1.56 (s, 9 H), 1.52 (s, 9H).

Compound XXX: 3-{[5-(2-guanidino-ethylcarbamoyl)-thiophene-2-carbonyl]-amino}-2-(pyrimidin-2-ylamino)-propionic acid bis trifluoroacetic acid salt.

With continued reference to Scheme K, to a solution of Compound XXIX: 3-{[5-(2-(N,N'-Bis-(BOC)-guanidino)-ethylcarbamoyl)-thiophene-2-carbonyl]-amino}-2-(pyrimidin-2-ylamino)-propionic acid methyl ester (100 mg, 0.16 mmol) in THF/water (4:1, 5 mL) was added lithium hydroxide monohydrate (10 mg, 0.24 mmol). The solution was stirred for 2 hours at room temperature after which the reaction was complete. The reaction mixture was concentrated under vacuum and the residue was acidified with 5% KHSO$_4$ solution. The mixture was then extracted with chloroform (4×) and the organic extracts were then washed with brine, dried (Na$_2$SO$_4$) and concentrated to the free acid as a white solid. This solid was then stirred in trifluoroacetic acid/dichloromethane (1:1, 10 mL) for 2 hours. The reaction mixture was concentrated to dryness and the residue was triturated with ether. The resulting solid Compound XXX was then dissolved in water, filtered and lyophilized to title compound as a white solid (54 mg, 52%). $^1$H NMR (400 MHz, DMSO) δ: 8.79 (t, 1 H), 8.78 (t, 1 H), 8.29 (d, 2 H), 7.69 (s, 2 H), 7.52 (br t, 1 H), 7.29 (d, 1 H), 6.64 (t, 1 H), 4.53 (q, 1 H), 3.71 (t, 2H), 3.37 (m, 2 H), 3.30 (m, 2 H).

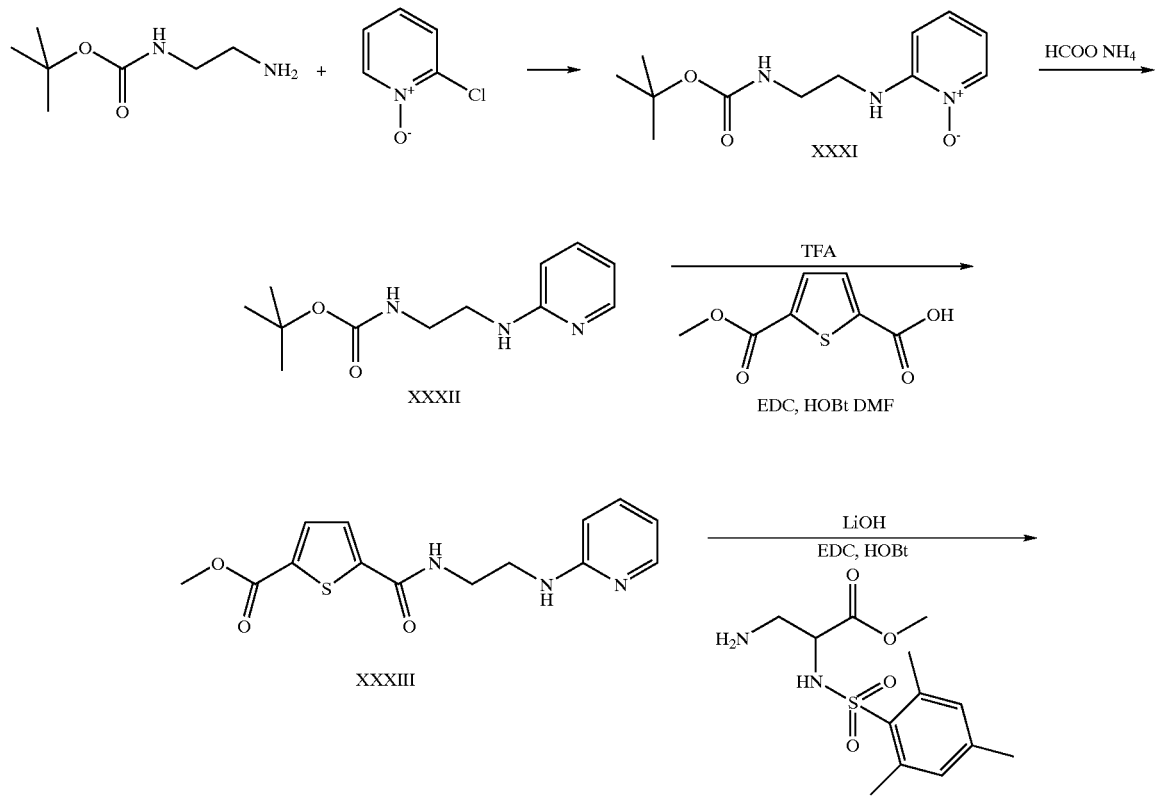

SCHEME L

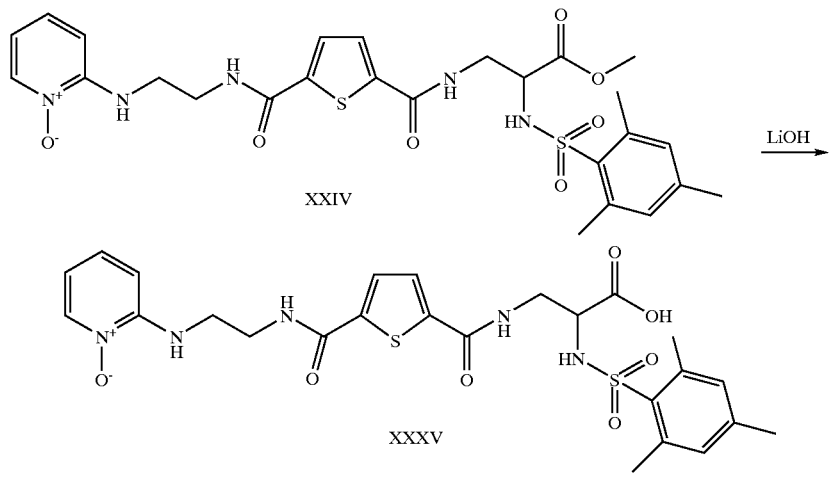

Compound XXXI: [2-(1-Oxy-pyridin-2-ylamino)-ethyl)]-carbamic acid tert-butyl.

To a solution of (2-Amino-ethyl)-carbamic acid tert-butyl ester (130 mg, 0.85 mmol) in n-butanol (40 mL) was added a mixture of 2-chloropyridine N-oxide (142 mg, 0.86 mmol) and DIEA (0.31 mL, 1.8 mmol). The reaction mixture was refluxed at 110° C. for 14 hrs. The solvent was evaporated and the residue was purified on silica gel using 30% Methanol/EtOAc as eluant. This gave 190 mg (91%) of pure [2-(1-Oxy-pyridin-2-ylamino)-ethyl)]-carbamic acid tert-butyl. $^1$HNMR (300 MHz, CD$_3$OD) δ: 2.44(s, 9H), 3.30 (t, 2H), 3.50 (t, 2H), 6.77(t, 1H), 7.02(m, 1H), 8.10(d, 1H), 8.55 (m, 1H).

Compound XXXII: [2-(Pyridin-2-ylamino)-ethyl]-carbamic acid tert-butyl ester.

To a solution of [2-(1-Oxy-pyridin-2-ylamino)-ethyl)]-carbamic acid tert-butyl (90 mg, 0.36 mmol) in methanol (25 mL) was added ammonium formate (25 mg, 0.37 mmol) and Pd/C under a stream of nitrogen. The reaction mixture was stirred overnight. The catalyst was filtered and the solvent was evaporated under reduced pressure. The residue was purified on silica gel using 10% Methanol/EtOAc as eluant. This gave 42 mg (50%) of pure [2-(Pyridin-2-ylamino)-ethyl]-carbamic acid tert-butyl ester. $^1$HNMR (300 MHz, CDCl$_3$) δ: 2.43(s, 9H), 3.40 (m, 2H), 3.48 (m, 2H), 6.42(d, 1H), 6.60(t, 1H), 7.42(t, 1H), 8.08 (bs, 1H).

Compound XXXIII: 5-[2-(Pyridin-2-ylamino)-ethylcarbamoyl]-thiophene-2-carboxylic acid methyl ester.

To a solution of [2-(Pyridin-2-ylamino)-ethyl]-carbamic acid tert-butyl ester (44 mg, 0.14 mmol) was mixed with a mixture of (1:1)TFA/CH$_2$Cl$_2$ (30 mL) and the reaction mixture was stirred at room temperature overnight. The solvent was evaporated and the residue was tritured with dry ether (2×30 mL). This gave 35 mg (95%) of pure trifluoroacetate salt. The salt was neutralized with DIEA and treated with mono methylthiophene dicarboxylic acid (32 mg, 0.17 mmol), hydroxybenzotriazole (24 mg, 0.17 mmol) in DMF (20 mL). To this mixture was added 1-(3-dimethylamino)propyl)-3-ethylcarbodiimide hydrochloride (33 mg, 0.17 mmol). The reaction was stirred overnight at room temperature. Insolubles were removed by filtration and the solvent was evaporated. Purification of the residue on silica gel (5% MeOH/EtOAc) gave 38 mg (88%) of pure 5-[2-(Pyridin-2-ylamino)-ethylcarbamoyl]-thiophene-2-carboxylic acid methyl ester. $^1$HNMR (300 MHz, CDCl$_3$) δ: 3.43 (m, 2H), 3.51 (m, 2H), 3.92 (s, 3H), 6.45(d, 1H) 6.80(t, 1H), 7.42(t, 1H), 7.45 (s, 1H), 7.55 (s, 1H), 8.10 (s, 1H).

Compound XXXIV: 3-({5-[2-(Pyridin-2-ylamino)-ethylcarbamoyl]-thiophene-2-carbonyl}-amino)-2-(2,4,6-trimethyl-benzenesulfonylamino)-propionic acid methyl ester.

5-[2-(Pyridin-2-ylamino)-ethylcarbamoyl]-thiophene-2-carboxylic acid methyl ester was hydrolyzed with LiOH as described before. To a mixture of 5-[2-(Pyridin-2-ylamino)-ethylcarbamoyl]-thiophene-2-carboxylic acid (38 mg, 0.12 mmol), salt of 3-amino-2-(2,4,6-trimethyl-benzenesulfonylamino)-propionic acid 2-tert-butoxycarbonylamino-ethyl ester (47 mg, 0.14 mmol), hydroxybenzotriazole (21 mg, 0.15 mmol) in DMF (20 mL), was added 1-(3-dimethylamino) propyl)-3-ethylcarbodiimide hydrochloride (29 mg, 0.15 mmol). The reaction was stirred overnight at room temperature. Insolubles were removed by filtration and the solvent was evaporated. Purification of the residue on silica gel (10% MeOH/EtOAc) gave 60 mg (87%) of pure 3-({5-[2-(Pyridin-2-ylamino)-ethylcarbamoyl]-thiophene-2-carbonyl}-amino)-2-(2,4,6-trimethyl-benzenesulfonylamino)-propionic acid methyl ester. $^1$HNMR (300 MHz, CDCl$_3$) δ: 2.22 (s, 3H), 2.61 (s, 6H), 3.55 (m, 4H), 3.82 (m, 1H), 4.09 (m, 1H), 6.50(d, 1H), 6.69(t, 1H), 6.90(s, 2H), 7.05(t, 1H), 7.40(m, 3H), 8.10 (s, 1H), 8.43(m, 1H).

Compound XXXV: 3-({5-[2-(Pyridin-2-ylamino)-ethylcarbamoyl]-thiophene-2-carbonyl}-amino)-2-(2,4,6-trimethyl-benzenesulfonylamino)-propionic acid acetic acid salt.

A mixture of 3-({5-[2-(Pyridin-2-ylamino)-ethylcarbamoyl]-thiophene-2-carbonyl}-amino)-2-(2,4,6-trimethyl-benzenesulfonylamino)-propionic acid methyl ester (40 mg, 0.069 mmol), lithium hydroxide (34 mg, 1.39 mmol), in acetonitrile (10 mL) was stirred for 4 hrs at room temperature. The solvent was removed and the crude reaction product was taken up in ethyl acetate (40 mL). The solution was neutralized with acetic acid (1.0 mL). Solvent was than dried over sodium sulfate and evaporated. Purification of the residue on silica gel (10% MeOH-EtOAc) gave 40 mg of pure acetic acid salt of 3-({5-[2-(Pyridin-2-ylamino)-ethylcarbamoyl]-thiophene-2-carbonyl}-amino)-2-(2,4,6-trimethyl-benzenesulfonylamino)-propionic acid (86%). $^1$HNMR (300 MHz, CD$_3$OD) δ: 2.22 (s, 3H), 2.61 (s, 6H), 3.57 (m, 4H), 3.82 (m, 2H), 6.50(d, 1H), 6.69(m, 2H), 6.90(s, 2H), 7.42(m, 3H), 8.01 (m, 1H).

Scheme M

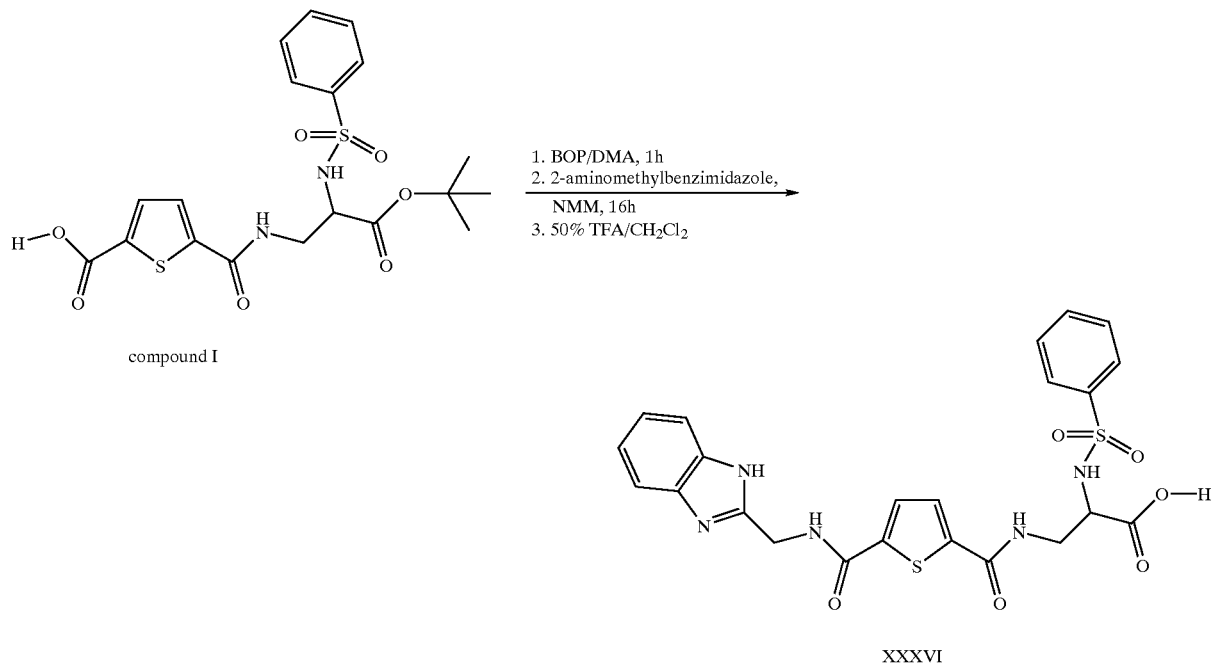

Compound XXXVI: 2-Benzenesulfonylamino-3-({5-[(1H-benzoimidazol-2-ylmethyl)-carbamoyl]-thiophene-2-carbonyl-amino)-propionic acid.

compound I (4.79 g, 10.54 mmol) in dry DMA (20 mL) was treated with BOP at room temperature under N2. After 1 h, 2-aminomethylbenzimidazole dihydrochloride and NMI (2.5 mL, 31.6 mmol) in DMA (25 mL) were added and the reaction mixture was stirred at room temperature for 16 h. DMA was removed under reduced pressure and the residue was extracted with ethyl acetate and the organic extracts were washed with $H_2O$ and saturated $NaHCO_3$, dried over $MgSO_4$, filtered and concentrated. The crude material was purified by chromatography on flash Silica eluting with $CH_2Cl_2$ to 5% MeOH/$CH_2Cl_2$ to give 5.23 g of the t-butyl ester (52% yield). $^1$H-NMR (400 MHz, DMSO-$d_6$): 9.34 (t, 1H), 8.70 (t, 1H), 8.40 (d, 1H), 7.78 (m, 3H), 7.58 (m, 6H), 7.14 (m, 2H), 4.67 (d, 2H), 4.03 (m, 2H), 3.40 (m, 1H), 1.12 (s, 9H).

The t-butyl ester (3.73 g) was treated with 50% TFA/$CH_2Cl_2$ (40 mL) and the progress of the reaction was followed by TLC. After 3 h, the reaction mixture was taken to dryness under reduced pressure and the residue was triturated from ether then recrystalised from methanol/ether to give 2.24 g of compound XXXVI (58% yield). $^1$H-NMR (400 MHz,$CD_3$-OD): 7.85–7.44 (m, 11H), 5.04 (s, 2H), 4.21 (m, 1H), 3.74 (m, 1H), 3.49 (m, 1H).

SCHEME N

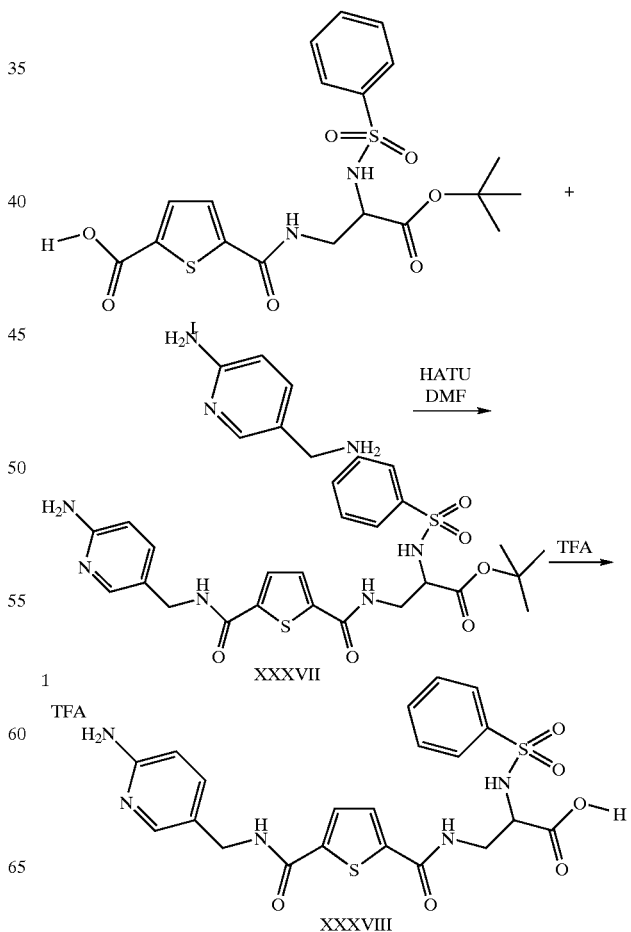

Compound XXXVII: 3-({5-[(6-Amino-pyridin-3-ylmethyl)-carbamoyl]-thiophene-2-carbonyl}-amino)-2-benzenesulfonylamino-propionic acid tert-butyl ester.

HATU (200 mg, 0.52 mmol) was added in one portion at room temperature to a solution of 5-(2-Benzenesulfonylamino-2-tert-butoxycarbonyl-ethylcarbamoyl)-thiophene-2-carboxylic acid (200 mg, 0.42 mmol) dissolved in anhydrous DMF with 5-Aminomethyl-pyridin-2-ylamine (Dong-Mei Feng et al.; J. Med. Chem. (1997), 40, 3726) (200.0 mg, 1.63 mmol) and triethyl amine (200 µl). This reaction mixture was left stirring at room temperature for 12 hours then the DMF was evaporated and the residue was purified via flash chromatography on silica gel using first ethyl acetate to flush-out undesired material then methanol:ethyl acetate (1:4) to give compound XXX-VII as a pure yellow solid after evaporation of the solvent. (HNMR, 400 MHz, CD3OD) δ: 7.98 (d, 1H), 7.80 (m, 2H), 7.56–7.43 (m, 7H), 7.32 (m, 1H), 6.50 (d, 2H), 4.90 (bs, 2H), 4.36 (d, 2H), 4.09–4.03 (m, 1H), 3.60 (m, 1H), 3.52 (m, 1H), 1.25 (s, 9H).

Compound XXXVIII: 3-({5-[(6-Amino-pyridin-3-ylmethyl)-carbamoyl]-thiophene-2-carbonyl}-amino)-2-benzenesulfonylamino-propionic acid trifluoroacetic acid salt.

Compound XXXVII (30 mg, 0.053 mmol) was dissolved in dichloromethane (2.0 mL) then at room temperature trifluoroacetic acid was added to this solution which was then left stirring over nigth. Evaporation of the solvents followed by trituration of the resulting residue with anhydrous diethyl ether filtration gave a solid which was washed twice with dichloromethane then dried under vaccuum to give 28 mg of compound XXXVII as a beige powder. (HNMR, 400 MHz, CD3OD) δ: 7.97 (dd, 1H), 7.84 (m, 3H), 7.64 (d, 1H), 7.58 (d, 1H), 7.53–7.44 (m, 3H), 7.03 (d, 1H), 4.45 (s, 2H), 4.18 (dd, 1H), 3.74 (dd, 1H), 3.49 (dd, 1H).

Scheme O

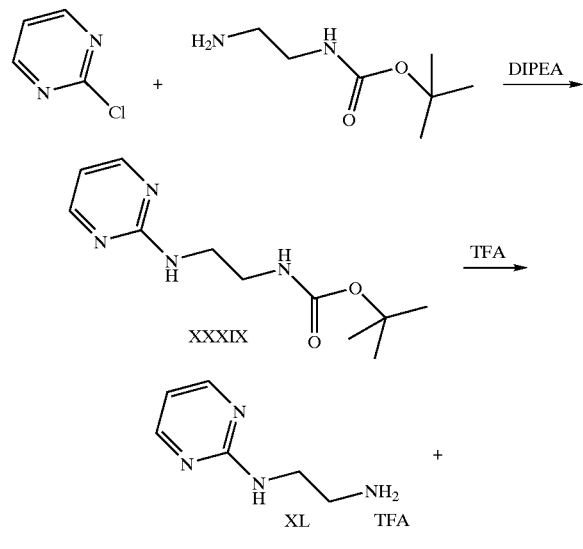

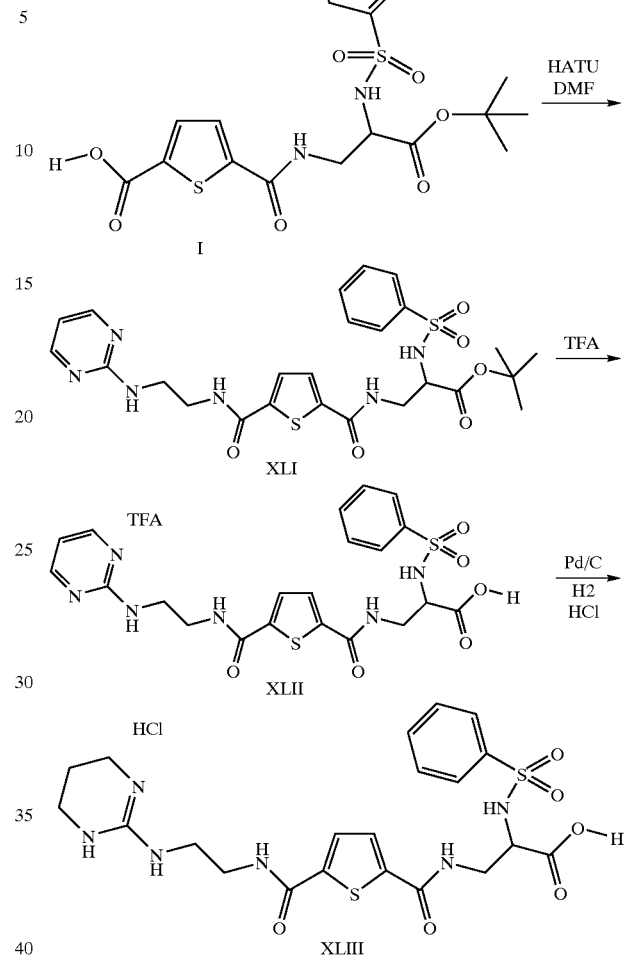

Compound XXXIX: [2-(Pyrimidin-2-ylamino)-ethyl 3-carbamic acid-tert-butyl ester.

(2-Amino-ethyl)-carbamic acid tert-butyl ester (2.0 g, 0.013 mol) was haled 12 hours between 65–75 C along with chloropyrimidine (1.0 g, 2.25 mmol) and diisopropyl ethyl amine (1.5 mL) in anhydrous tetrahydrofuran (1.0 mL). The reaction mixture was concentrated and the resulting residue was purified on silica gel using a ethyl acetate, hexane (1:1) mixture of eluent providing 1.5 g compound XXXIX as a white powder. HNMR (400 MHz, CDCl₃) δ: 8.35 (m, 2H), 6.59 (t, 1H), 5.81 (bs, 1H), 5.12 (bs, 1H), 3.58 (m, 2H), 3.38 (m, 2H), 1,45 (s, 9H).

Compound XL: N,1-Pyrimidin-2-yl-ethane-1,2-diamine trifluoroacetic acid salt.

2-(Pyrimidin-2-ylamino)-ethyl]-carbamic acid-tert-butyl ester (900 mg, 3.8 mmol) was dissolved in anhydrous dichloromethane (5.0 mL), trifluoroacetic acid (5.0 mL) was added to the mixture which was then left stirring at room temperature for 12 hours. The solvents were evaporated under reduced pressure and the resulting yellow oil was mixed with anhydrous diethyl ether, the ether layer was separated then discarded and the yellow oil was left under vaccum to crystallize providing 1.08 g of compound XL as a yellow powder. HNMR (400 MHz, DMSO, d6) δ: 8.35 (m, 2H), 7.86 (bs, 3H), 7.39 (bs, 1H), 6.68 (t, 1H), 3.52 (m, 2H), 3.00 (m, 2H).

Compound XLI: 2-Benzenesulfonylamino-3-({5-[2-(pyrimidin-2-ylamino)-ethylcarbamoyl]-thiophene-2-carbonyl}-amino)-propionic acid tert-butyl ester.

HATU (241.7 mg, 0.636 mmol) was added in one portion at room temperature to a solution of 5-(2-Benzenesulfonyl-amino-2-tert-butoxycarbonyl-ethylcarbamoyl)-thiophene-2-carboxylic acid (200 mg, 0.424 mmol) dissolved in anhydrous DMF (5.0 mL) with N,1-Pyrimidin-2-yl-ethane-1,2-diamine trifluoroacetic acid salt (Dong-Mei Feng et al.; J. Med. Chem. (1997), 40, 3726) (232 mg, 0.636 mmol) and diisopropylethylamine (500 µL). This reaction mixture was left stirring at room temperature for 1 hour then water was added and this mixture was extracted with ethyl acetate, the organic phase was separated dried ($Na_2SO_4$), filtered, then concentrated and the resulting residue was purified via flash chromatography on silica gel using first ethyl acetate to flush-out undesired material then methanol:ethyl acetate (1:9) to compound XLI as a pure white powder after evaporation of the solvent. (HNMR, 400 MHz, DMSO, d6) δ: 8.72 (m, 1H), 8.68 (m, 1H), 8.39 (d, 1H), 8.27 (d, 2H), 7.77 (m, 2H), 7,67 (d, 1H), 7.62–7.51 (m, 4H), 7.23 (m, 1H), 6.58 (t, 1H), 4.03 (m, 1H), 3.42 (m, 6H), 1.12 (s, 9H).

Compound XLII: 2-Benzenesulfonylamino-3-({5-[2-(pyrimidin-2-ylamino)-ethylcarbamoyl]-thiophene-2-carbonyl}-amino)-propionic acid trifluoroacetic acid salt.

Compound XLI (160 mg, 0.278 mmol) was dissolved in anhydrous dichloromethane (2 mL). To this solution at room temperature was added trifluoroacetic acid and the reaction mixture was then stirred 12 hours. The reaction mixture was then concentrated under reduced pressure, the resulting residue was triturated in anhydrous diethyl ether then dried under vaccuum to give 200 mg of compound XLII contaminated with the solvent as a yellow oil. (HNMR, 400 MHz, DMSO, d6) δ: 8.73 (m, 1H), 8.62 (m, 1H), 8.35 (bs, 2H), 8.25 (d, 1H), 7.75 (m, 2H), 7.67–7.45 (m, 5H), 6.67 (m, 1H), 4.02 (m, 1H), 3.51–3.28 (m, 6H).

Compound XLIII: 2-Benzenesulfonylamino-3-({5-[2-(1,4,5,6-tetrahydro-pyrimidin-2-ylamino)-ethylcarbamoyl]-thiophene-2-carbonyl}-amino)-propionic acid, hydrochloride salt.

Compound XLII (200 mg, 0.316 mmol) was dissolved in acetic acid (10 mL) and hydrochloric acid (0.1 mL) then palladium on carbon 10% (200 mg) and the reaction mixture was pressurized with hydrogen (45–50 psi), stirred vigorously for 2 hours then the solution was filtered on celite. The solvents were evaporated under reduced pressure and the resulting residue was triturated in anhydrous diethyl ether and this white powder was purified on C8 Bond elute reverse phase using 10% acetonitrile in water as the eluent to provide 25 mg of material which was lyophilized in diluted hydrochloric acid providing 25 mg of compound XLIII as a white powder.

(HNMR, 400 MHz, $CD_3OD$) δ: 7.84 (dd, 1H), 7.65 (d, 1H), 7.59 (d, 1H), 7.54–7.45 (m, 3H), 4.21 (dd, 1H), 3.75 (dd, 1H), 3.55–3.45 (m, 3H), 3.38 (t, 6H), 1.96 (m, 2H).

EXAMPLE 2

Fibrinogen Binding to Immobilized GP IIb–IIIa ($\alpha_{IIb}\beta_3$) and $\alpha_v\beta_3$.

The wells of plastic microtiter plates were coated overnight at 4° C. with purified active $\alpha_{IIb}\beta_3$ (Calbiochem) or placental $\alpha_v\beta_3$ at 0.5 ug/mL (100 uL/well) in a buffer containing 150 mM NaCl, 20 mM Tris, pH 7.4, 1 mM $MgCl_2$, 0.2 mM $MnCl_2$, and including 1 mM $CaCl_2$ for $\alpha_{IIb}\beta_3$. Blocking of nonspecific sites was achieved by incubating the wells with 35 mg/mL bovine serum albumin (BSA) for at least 2 hours at 37° C. Biotinylated-fibrinogen (10 nM) was added in 0.2 mL binding buffer (100 mM NaCl, 50 mM Tris, pH 7.4, 1 mM $MgCl_2$, 0.2 mM $MnCl_2$ and 1 mg/mL BSA including 1 mM $CaCl_2$ for $\alpha_{IIb}\beta_3$) to the wells in triplicate in the absence or presence of increasing concentrations of compounds of interest (0.001–100 uM) and further incubated for 2 hours at 37° C. Nonbound fibrinogen was removed by five washes with binding buffer. Avidin conjugated to alkaline phosphatase (Sigma), diluted in binding buffer, was added and incubated for two hours at 37° C. The plates were washed five times with binding buffer, and after addition of the substrate PNPP (Pierce), the enzyme activity was measured by the absorbance at 405 nm. The concentration of inhibitor required to inhibit 50% of biotinylated-fibrinogen binding was defined as $IC_{50}$ determined by a nonlinear, sigmoidal dose response variable slope from the GraphPad Prism software. The results of the $\alpha_v\beta_3$ and $\alpha_{IIb}\beta_3$ assays are reported in Table 1.

TABLE 1

$IC_{50}$ values for the fibrinogen binding assay.

| CMPD # | Structure | $IC_{50}$ $\alpha_v\beta_3$ (µM) | $IC_{50}$ $\alpha_{IIb}\beta_3$ (µM) |
|---|---|---|---|
| VII | 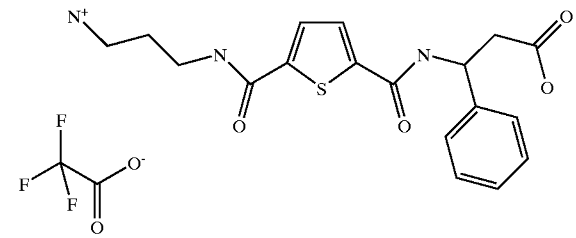 | 6.6 | 13.7 |

TABLE 1-continued

IC$_{50}$ values for the fibrinogen binding assay.

| CMPD # | Structure | IC$_{50}$ $\alpha_v\beta_3$ ($\mu$M) | IC$_{50}$ $\alpha_{IIb}\beta_3$ ($\mu$M) |
|---|---|---|---|
| VIII | 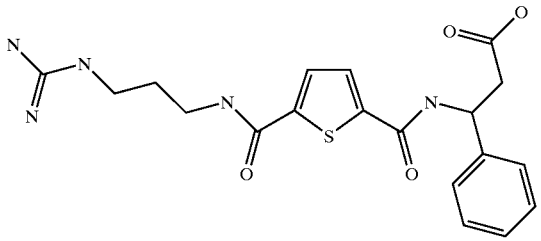 | 3.2 | 5.9 |
| XI | 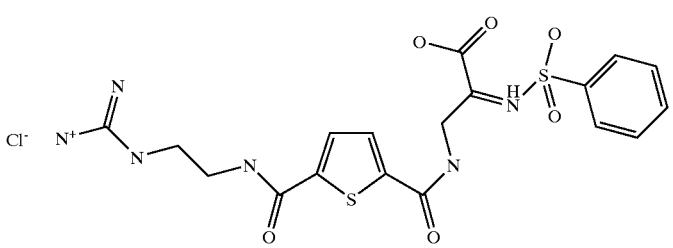 | .00058 | .00031 |
| XXI | 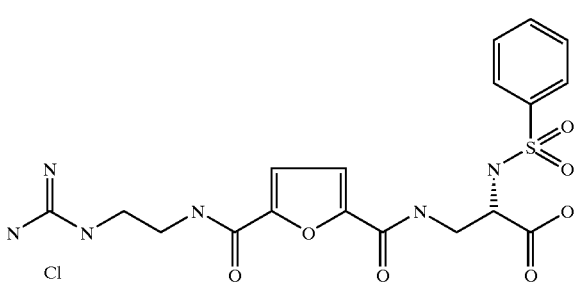 | 0.045 | 0.931 |
| XXX | 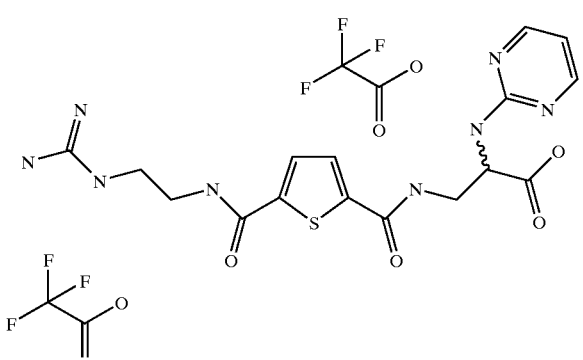 | 0.15 | 0.69 |

EXAMPLE 3

Cell Adhesion Assay.

The wells of 96-well plates (Immunolon) were coated, by incubation overnight at 4° C., with 5 ug/mL vitronectin, 2 ug/mL osteopontin, or fibronectin or 10 mg/mL BSA in PBS. The protein solution was flicked out and the wells were blocked with 10 mg/mL BSA (0.1 mL) for 1–2 hours at 37° C. Cells HT29, K562, or K562 transfected with $\alpha_v\beta_3$ (Blystone et al., 1994) were loaded with a fluorescent marker, 5-chloromethylfluorescein diacetate (Molecular Probes, Eugene, Oreg.) for 1 hour at 37° C., then incubated in fresh medium without the fluorescent marker for 1 hour. Cells were lifted with trypsin-EDTA and washed two times with Hank's balanced salt solution minus cations (Sigma) supplemented with 1 mM MgCl$_2$ Cells (75,000 cells/well) were added to coated plates in triplicate and allowed to attach at 37° C. for 1 hour in the presence or absence of specific antibodies (5 ug/mL) or 10-fold dilutions of compounds of interest starting at 10 uM. Nonadherent cells were removed by gentle washing twice with PBS. The adherent cells were solubilized with 1% triton x-100 and detected using a fluorescence plate reader (DYNEX Technologies). The number of attached cells was calculated based upon standard curves for each cell line used in the experiment. Non-specific cell attachment (attachment to wells coated with BSA) was always less than 5%. The results are presented in Table 2.

TABLE 2

IC$_{50}$ values for the cell adhesion assay.

| Compound | IC$_{50}$ ($\mu$M) K562-tr Osteopontin ($\alpha_v\beta_3$) | IC$_{50}$ ($\mu$M) HT29 Vitronectin ($\alpha_v\beta_5$) | IC$_{50}$ ($\mu$M) K562 Fibronectin ($\alpha_5\beta_1$) |
|---|---|---|---|
| VII | >10 | >10 | >10 |
| X | >10 | >10 | >10 |
| XI | 0.087 | 0.21 | 5.3 |
| XIX | 1.3 | 12 | >10 |
| XXI | 2.3 | 5.4 | >10 |
| XXX | 3.4 | >10 | >10 |

EXAMPLE 4

Cell Proliferation and Cytotoxicity MTT Assay

The wells of microtiter plates were seeded with 2000 cells/well T24, 2500 cells/well HT29 or 5000 cells/well HMVEC (Cell Systems) in 100 uL, followed by an overnight culture for cell adhesion. The next day, the media is supplemented with 100 uL of 10-fold dilution of compound of interest starting at 10 uM. Following culture for 72 hours, 3-(4,5-dimethyl-2-thiazolyl)-2,5-diphenyltetrazolium bromide (MTT; Sigma) at 2 mg/mL was added to each well (50 uL/well) and further incubated for 4 hours at 37° C. The medium was flicked out and 200 uL of a 1:1 solution of ethanol:acetone followed by 25 uL of glycine buffer (0.1 M glycine, 0.1M NaCl, pH 10.5) is added and the color measured by the absorbance at 570 nm. The results are presented in Table 3.

TABLE 3

Cytotoxicity Assay

| Compound number | IC$_{50}$ (uM) HMVEC | IC$_{50}$ (uM) HT29 |
|---|---|---|
| VII | >10 | >10 |
| VIII | >10 | >10 |
| XI | 0.87 | 9.9 |
| XXI | 8.9 | >10 |
| XXX | >10 | >10 |

EXAMPLE 5

Chick Chorioallantoic Membrane (CAM)
A) Shell-Less Embryo Culture

Fertilized white leghorn chicken eggs (SPAFAS Inc., Norwich, Conn.) were received at day 0 and incubated for 3 days at 37 C with constant humidity. On day 3, eggs were rinsed with 70% ethanol and opened into 100 mm$^2$ tissue culture coated Petri dishes under aseptic conditions. The embryos were then returned to a humidified 38 C incubator for 7–9 additional days.
B) Mesh Assay Vitrogen (Collagen Biomaterials, Palo Alto, Calif.) at a final concentration of 0.73 mg/mL and Matrigel (Becton Dickinson, Bedford, Mass.) at a final concentration of 10 mg/mL was directly pipetted onto Nylon meshes with 250 $\mu$m$^2$ openings which were cut into 4 mm×4 mm squares and autoclaved. Polymerization of meshes were under aseptic conditions, on bacteriological Petri dishes. The polymerization conditions for each substrate were identical; after mixing with or without 250 $\mu$g of VPF/VEGF$_{165}$ (Peprotech, Rocky Hill, N.J.) and/or compounds of interest, 40 $\mu$L were pipetted onto each mesh in a bacteriological Petri dish. The Petri dish was placed in a humidified 37 C incubator with 5% CO$_2$ for 30 minutes to allow polymerization followed by an incubation at 4° C. for 2 hours.

In a tissue culture enclosure, meshes were placed onto the periphery of the CAM of a day 12–14 embryo, excluding areas containing major vessels. The embryos were then returned to the humidified 38° C. incubator with 3% CO$_2$ for 24 to 48 additional hours.
C) Visualization and Quantification of Vessels Embryos were removed from the incubator and meshes were viewed under a dissecting microscope for gross evaluation. Injection of 400 $\mu$L FITC dextran, MW 2,000,000 (Sigma, St. Louis, Mo.) through glass microcapillary tubes by infusion into the umbilical vein was performed at a rate of 200 $\mu$l per minute. The FITC dextran was allowed to circulate for 5 minutes and 3.7% formaldehyde in PBS was applied directly on each mesh. The embryos were then incubated at 40° C. for 5 minutes and the meshes were dissected off the CAM and fixed in 3.7% formaldehyde for 10 minutes to overnight.

After fixation, meshes were mounted on slides with 90% glycerol in PBS and visualized on an inverted fluorescence microscope. A Nikon Diaphot with a Sony DXC-151A camera attached to the side port was used for capture of images and analysis was with the NIH Image 1.61 software program. For each mesh, 5 random staggered images (approximately 600 $\mu$m each) were captured. The areas of high intensity were highlighted and measured. Results are expressed as ability to suppress capillary formation after subtraction from negative control. Values were calculated as a inhibition, considering 100% the capillary density achieved by VPF in the presence of vitrogen alone minus the bakground levels in the absence of VPF. Negative values indicated angiogenic stimulation above the VPF positive control. Results for the cam assay showed significant inhibition values for the compounds tested.

TABLE 4

CAM Assay

| Compound number | % of inhibition at 33 $\mu$g/mesh in the presence of VEGF* |
|---|---|
| VII | 34% |
| VIII | 36% |
| XI | 38% |
| XVIII | 20% |
| XIX | 8% |
| XXX | 31% |
| XXI | 32% |

*significant if >25%

EXAMPLE 6

Mouse Matrigel Angiogenesis Assay

To examine VEGF driven angiogenesis, cells expressing murine VEGF (SK-MEL2-V+) or vector alone (SK-MEL2) were collected by treatment of culture flasks with trypsin, and resuspended to a concentration of 1×107 cells in 0.6 mL in serum free media. The cell suspension was mixed gently with 1.4 mL Matrigel (Collaborative Biomedicals) and loaded in syringes. Alternatively, to examine FGF driven angiogenesis, matrigel was mixed with 500 ng bFGF with 1 U heparin. The matrigel suspensions were injected into mice subcutaneously, 200 uL per injection, on each side midway between the flank and the shoulder blades. Compounds of interest were injected at varying doses e.g., 1, 5 or 10 mg/kg/day. Animals were injected with 100 uL of the compound dissolved with sterile saline, in the back of the neck.

Mice (5 animals/group) were anaesthesized with avertin after 4 to 6 days of treatment, and a cardiac perfusion with FITC-dextran (M.W. 2,000,000) was performed to label vessels in the matrigel plugs. Matrigel/skin were fixed in situ followed by whole mount cross sections and analyzed by confocal microscopy. For immunohistochemistry, the pellets were collected with the overlying skin and placed in Histoprep (10% formalin in PBS) for 2 hours and then transferred to PBS for 3–4 hours followed by 70% ethanol and storage at 4° C. until processing for parrafin sections. Sections were examined by immunohistochemistry for von Willebrand factor VIII and PECAM-1 using the appropriate antibodies.

EXAMPLE 7

Inhibition of Metastasis in Angiomouse/Metamouse Human Lung Cancer Model of H460

Male and female athymic BALB/c nude mice between 4 and 5 weeks of age were used. The animals were bred and maintained in an HEPA-filtered environment with cages, food and bedding sterilized by autoclaving. The breeding pairs were obtained from the Charles River Laboratories (Wilmington, Mass.). The animal diets were obtained from Harlan Teklab (Madison, Wis.). Ampicillin (Sigma, St Louis, Mo.) 5.0% (v/v) was added to the autoclaved drinking water.

Compound VII was tested and AGM-1470 (chloroacetyl-(3R,4S,5S,6R)-5-methoxy-4-[(2R,3R)-2-methyl-3-(3-methyl-2-butenyl)oxiranyl]-1-oxaspiro[2.5]oct-6-yl ester carbamic acid) was used as a positive control.

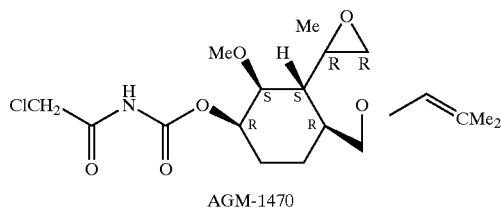

AGM-1470

The compounds were dissolved using PEG400 with heating and sonicatin. The solutions were then diluted with saline to obtain the desired concentrations (30%/70%) and stored at −20° C.

Human non small-cell lung cancer cell line H460 with expression of green fluorescent protein was obtained from the National Cancer Institute. The cells were transfected with vectors carrying the green fluorescent protein (GFP) gene. The cell line was propagated by subcutaneous implantation in nude mice.

Test animals were transplanted by surgical orthotopic implantation (SOI) using fragments harvested from subcutaneaous tumor stock animals. The animals were anesthetized with isoflurane and the surgical area was sterilized using iodine solution and alcohol. A left thoracotomy was made along the 4$^{th}$ intercostal space using a pair of scissors. Two pieces of H460 tumor tissue of one cubic millimiter each were sutured to the left lung using an 8-0 nylon surgical suture. The thorax was closed using a sterile 6-0 silk suture. A sterile 3-cc syringe with a 25-gauge needle was used to remove the air and inflate the lung. All surgical and animal manipulations and procedures were conducted under HEPA-filtered laminar flow hoods.

Extra numbers of mice were transplanted to compensate for postsurgical losses. The orthotopically transplanted animals used were selected to establish groups of similar mean body weight. Groups for each of the cohort conditions wre randomly chosen. The cohort was grouped as follows. A total of 10 mice were used for each dosage regimen. Administration of test compounds and vehicle by subcutaneous injection was begun three days after the orthotopic implantation.

TABLE 5

Study design for the inhibition of metastasis in angiomouse/metamouse human lung cancer model of H460.

| Group | Compound | Dose | Route | Schedule |
|-------|----------|------|-------|----------|
| A | vehicle | 0.1 mL/mouse | SC | 2 times/day |
| B | AGM-1470 | 10 mg/kg | SC | 3 times/week |
| C | VII | 5 mg/kg | SC | 2 times/day |
| D | VII | 50 mg/kg | SC | 2 times/day |

Two animals for each treatment group were sacrificed at day-14 after orthotopic implantation of H460. The remaining animals for each group were sacrificed at day-28 after implantation. The sacrificed animals were evaluated for primary and secondary tumors. Gross examination for distant metastasis was conducted at necropsy. Tissue samples of the primary tumor and those from relevant organs such as the lung, the liver and the lymph nodes wre processed through standards procedures of hematoxylin and eosin staining for subsequent microscopic examination.

The mediastinal lymph nodes, the liver and the lung in each animal were collected. The sampled tissues were sectioned and stained, then microscopically examined. The fisher-exact test was performed to compare distant metastasis to these organs in the treated and the controls. Group D had no lung metastasis. The results are shown below.

TABLE 6

Efficacy of compounds on metastasis.

| Gr | No. of animals available for pathology | Incidence of lymph node metastasis | P-value vs control | Incidence of lung metastasis | P-value vs control |
|----|---|---|---|---|---|
| A | 9 | 3/9 | — | 5/9 | — |
| B | 10 | 1/10 | 0.303 | 3/10 | 0.370 |
| C | 10 | 2/10 | 0.608 | 1/10 | 0.057 |
| D | 10 | 3/10 | 1 | 0/10 | 0.011 |

While particular embodiments of the invention have been described, it will also be apparant to these of ordinary skill in the art that various modifications, including the preparation of certain analogs, can be made without departing from the spirit and scope of the invention. Accordingly, it is not intended that the invention be limited except by the appended claims.

We claim:
1. A compound of the formula:

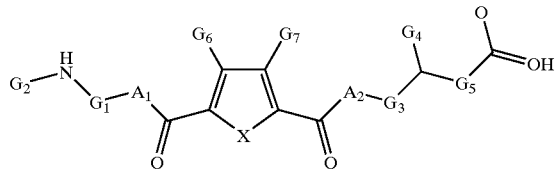

wherein X is selected from the group consisting of O and S; wherein $A_1$ and $A_2$ are individually selected from the group consisting of O, S and NH;
wherein $G_1$, and $G_3$ are $C_{1-4}$ alkyl chains;
wherein $G_5$ is a $C_{0-4}$ alkyl chain; and
wherein $G_2$ is H or

wherein $A_3$ is O or NH and $A_4$ is $NH_2$;
wherein $G_4$ is a $C_{5-8}$ aryl, a $C_{5-8}$ arylsulfonylamino, an $C_{5-8}$ arylamino; and
wherein $G_6$ and $G_7$ are individually selected from the group consisting of H, F, Cl, I, Br and a $C_{1-4}$ alkyl, or a salt, ester, or salt of an ester thereof.
2. The compound of claim 1, wherein X is S.
3. The compound of claim 1, wherein X is O.
4. The compound of claim 1, wherein $A_1$ is NH.
5. The compound of claim 1, wherein $A_1$ is O.
6. The compound of claim 1, wherein $A_2$ is NH.
7. The compound of claim 1, wherein $A_2$ is O.
8. The compound of claim 1, wherein $G_1$ is a $C_1$ alkyl.
9. The compound of claim 1, wherein $G_1$ is —(CH$_2$)$_0$—.
10. The compound of claim 1, wherein $G_1$ is a $C_2$ alkyl.
11. The compound of claim 1, wherein $G_1$ is a $C_3$ alkyl.
12. The compound of claim 1, wherein $G_3$ is a $C_1$ alkyl.
13. The compound of claim 1, wherein $G_3$ is a $C_2$ alkyl.
14. The compound of claim 1, wherein $G_5$ is a $C_1$ alkyl.
15. The compound of claim 1, wherein $G_5$ is a $C_2$ alkyl.
16. The compound of claim 1, wherein $G_2$ is

wherein $A_3$ is O or NH and $A_4$ is $NH_2$.
17. The compound of claim 1, wherein —NH-$G_1$ forms a urea moiety.
18. The compound of claim 1, wherein $G_4$ is phenylsulfonylamino.
19. The compound of claim 1, wherein $G_4$ is phenyl.
20. The compound of claim 1, wherein $G_6$ and $G_7$ are halogens.
21. The compound of claim 1, wherein $G_6$ and $G_7$ are the same.
22. The compound of claim 1, wherein $G_6$ or $G_7$ are F.
23. A compound according to claim 1, wherein said compound is of the formula:

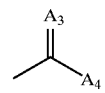

wherein X is selected from the group consisting of O and S;
$G_1$ and $G_3$ are $C_{1-4}$ alkyl chains;
$G_2$ is H or

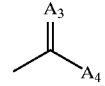

wherein $A_3$ is O or NH and $A_4$ is $NH_2$;
wherein $G_4$ is a $C_{5-8}$ aryl, a $C_{5-8}$ arylsulfonylamino, or a $C_{5-8}$ arylamino; and
wherein $G_6$ and $G_7$ are individually selected from the group consisting H, F, Cl, I, Br and a $C_{1-4}$ alkyl, or a salt, ester, or salt of an ester thereof.
24. The compound of claim 23, wherein X is S.
25. The compound of claim 23, wherein X is O.
26. The compound of claim 23, wherein $G_1$ is a $C_1$ alkyl.
27. The compound of claim 23, wherein $G_1$ is a $C_2$ alkyl.
28. The compound of claim 23, wherein $G_3$ is a $C_1$ alkyl.
29. The compound of claim 23, wherein $G_3$ is a $C_2$ alkyl.
30. The compound of claim 23, wherein $G_2$ is

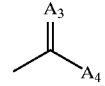

wherein $A_3$ is O or NH and $A_4$ is $NH_2$.
31. The compound of claim 23, wherein —NH-$G_2$ forms a urea moiety.
32. The compound of claim 23, wherein $G_4$ is phenylsulfonylamino.
33. The compound of claim 23, wherein $G_4$ is phenyl.
34. A method of treating foot and mouth disease comprising administering a pharmaceutically effective amount of the compound of claim 1 to a patient.
35. A method of treating osteoporosis comprising administering a pharmaceutically effective amount of the compound of claim 1 to a patient.
36. A method of treating restenosis comprising administering a pharmaceutically effective amount of the compound of claim 1 to a patient.
37. A method of treating ocular diseases comprising administering a pharmaceutically effective amount of the compound of claim 1 to a patient.
38. A method of treating heart diseases comprising administering a pharmaceutically effective amount of the compound of claim 1 to a patient.
39. A method of treating arthritis comprising administering a pharmaceutically effective amount of the compound of claim 1 to a patient.
40. A pharmaceutical composition comprising a pharmaceutically effective amount of a compound of claim 1, and a pharmaceutically acceptable carrier, diluent or adjuvant.

41. A compound selected from:

2-Benzenesulfonylamino-3-{[5(3-guanidino-propylcarbamoyl)-thiophene-2-carbonyl]-amino}-propionic acid, trifluoroacetic acid salt, 3-{[5-(3-guanidino-propylcarbamoyl)-thiophene-2-carbonyl]-amino}-3-phenyl-propionic acid, (2S)2-Benzenesulfonylamino-3-{[5-(2-guanidinyl-ethylcarbamoyl)-thiophen-2-carbonyl]-amino propionic acid hydrochloride salt, (2S)2-Benzenesulfonylamino-3-(5-[2-(3-benzyl-ureido)-ethylcarbamoyl]-thiophen-2-carbonyl-amino) propionic acid, 2S-Benzenesulfonylamino-3-[(5-hydrazinocarbonyl-thiophene-2-carbonyl)-amino]-3-propionic acid trifluoroacetate, 2S-Benzenesulfonylamino-3-[(5-guanidino-aminocarbonyl-thiophene-2-carbonyl)-amino]-3-propionic acid trifluoroacetate, (S)-3 -((5-(2-Amino-ethylcarbamoyl)-furan-2-carbonyl)-amino)-2-benzenesulfonylamino-propionic acid trifluoroacetate, (S)-2-Benzenesulfonylamino-((5-(2-guanidino-ethylcarbamoyl)-furan-2-carbonyl)-amino)-propionic acid hydrochloride, 3-{[5-(2-guanidino-ethylcarbamoyl)-thiophene-2-carbonyl]-amino}-2-(pyrimidin-2-ylamino)-propionic acid bis trifluoroacetic acid salt, 3-({5-[2-(Pyridin-2-ylamino)-ethylcarbamoyl]-thiophene-2-carbonyl}-amino)-2-(2,4,6-trimethyl-benzenesulfonylamino)-propionic acid acetic acid salt, 2-Benzenesulfonylamino-3-({5-[(1H-benzoimidazol-2-ylmethyl)-carbamoyl]-thiophene-2-carbonyl-amino)-propionic acid, 3-({5-[(6-Amino-pyridin-3-ylmethyl)-carbamoyl]-thiophene-2-carbonyl}-amino)-2-benzenesulfonylamino-propionic acid trifluoroacetic acid salt, 2-Benzenesulfonylamino-3-({5-[2-(1,4,5,6-tetrahydro-pyrimidin-2-ylamino)-ethylcarbamoyl]-thiophene-2-carbonyl}-amino)-propionic acid, hydrochloride salt, and salts, esters, and salts of esters thereof.

42. A method of treating metastasis comprising administering a pharmaceutically effective amount of the compound of claim 41 to a patient.

43. A method of inhibiting angiogenesis comprising administering a pharmaceutically effective amount of the compound of claim 41 to a patient.

44. A method of inhibiting fibronectin binding comprising administering a pharmaceutically effective amount of the compound of claim 41 to a patient.

45. A method of inhibiting osteopontin binding comprising administering a pharmaceutically effective amount of the compound of claim 41 to a patient.

46. A method of treating foot and mouth disease comprising administering a pharmaceutically effective amount of the compound of claim 41 to a patient.

47. A method of treating osteoporosis comprising administering a pharmaceutically effective amount of the compound of claim 41 to a patient.

48. A method of treating restenosis comprising administering a pharmaceutically effective amount of the compound of claim 41 to a patient.

49. A method of treating ocular diseases comprising administering a pharmaceutically effective amount of the compound of claim 41 to a patient.

50. A method of treating heart diseases comprising administering a pharmaceutically effective amount of the compound of claim 41 to a patient.

51. A method of treating arthritis comprising administering a pharmaceutically effective amount of the compound of claim 41 to a patient.

52. A method of treating diseases in which abnormal neovascularization occurs comprising administering a pharmaceutically effective amount of the compound of claim 41 to a patient.

53. A pharmaceutical composition comprising a pharmaceutically effective amount of a compound of claim 41, and a pharmaceutically acceptable carrier, diluent or adjuvant.

* * * * *

UNITED STATES PATENT AND TRADEMARK OFFICE
CERTIFICATE OF CORRECTION

PATENT NO. : 6,960,594 B2
APPLICATION NO. : 10/046396
DATED : November 1, 2005
INVENTOR(S) : Denis Labrecque It is certified that error appears in the above-identified patent and that said Letters Patent is hereby corrected as shown below:

Column 57, line 16 reads "wherein $G_1$ , and $G_3$ are $C_{1-4}$ alkyl chains;" should read -- wherein $G_1$ and $G_3$ are $C_{1-4}$ alkyl chains; --
Column 57, line 26 reads "wherein $G_4$ is a $C_{5-8}$ aryl, a $C_{5-8}$ arylsulfonylamino, an" should read -- wherein $G_4$ is a $C_{5-8}$ aryl, a $C_{5-8}$ arylsulfonylamino, a --
Column 57, line 56 reads "The compound of claim 1, wherein –NH-$G_1$ forms a" should read -- The compound of claim 1, wherein –NH-$G_2$ forms a --
Column 57, line 65 reads "The compound of claim 1, wherein $G_6$ or $G_7$ are F." should read -- The compound of claim 1, wherein $G_6$ or $G_7$ are F. --
Column 58, line 25 reads "group consisting H, F, Cl, I, Br, and a $C_{1-4}$ alkyl, or" should read -- group consisting of H, F, Cl, I, Br, and a $C_{1-4}$ alkyl, or --
Column 59, line 2 reads "2- Benzenesulfonylamino – 3 – {[5(3 – guanidino –" should read -- 2- Benzenesulfonylamino – 3 – {[5-(3 – guanidino – --
Column 59, line 8 reads "ethylcarbamoyl)-thiophen-2-carbonyl]-amino propi-" should read -- ethylcarbamoyl)-thiophen-2-carbonyl]-amino} propi- --
Column 59, line 31 reads "ylmethyl)-carbamoyl]-thiophene-2-carbonyl-amino) -" should read -- ylmethyl)-carbamoyl]-thiophene-2-carbonyl}-amino- --

Signed and Sealed this

Thirtieth Day of January, 2007

JON W. DUDAS
*Director of the United States Patent and Trademark Office*